US010065951B2

(12) United States Patent
Zhou et al.

(10) Patent No.: US 10,065,951 B2
(45) Date of Patent: Sep. 4, 2018

(54) SMALL MOLECULE TRANSCRIPTION MODULATORS OF BROMODOMAINS

(71) Applicant: Icahn School of Medicine at Mount Sinai, New York, NY (US)

(72) Inventors: Ming-MIng Zhou, Old Greenwich, CT (US); Guillermo Gerona-Navarro, New York, NY (US); Yoel Rodriguez-Fernandez, New York, NY (US); Patrizia Casaccia, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 15/314,959

(22) PCT Filed: May 29, 2015

(86) PCT No.: PCT/US2015/033178
§ 371 (c)(1),
(2) Date: Nov. 30, 2016

(87) PCT Pub. No.: WO2015/184257
PCT Pub. Date: Dec. 3, 2015

(65) Prior Publication Data
US 2017/0107218 A1 Apr. 20, 2017

Related U.S. Application Data

(60) Provisional application No. 62/005,645, filed on May 30, 2014.

(51) Int. Cl.
| C07D 471/04 | (2006.01) |
| A61K 31/437 | (2006.01) |
| A61K 45/06 | (2006.01) |
| C12N 5/079 | (2010.01) |
| C12N 5/071 | (2010.01) |

(52) U.S. Cl.
CPC .......... *C07D 471/04* (2013.01); *A61K 31/437* (2013.01); *A61K 45/06* (2013.01); *C12N 5/0602* (2013.01); *C12N 5/0622* (2013.01); *C12N 2501/999* (2013.01); *C12N 2506/30* (2013.01)

(58) Field of Classification Search
CPC .. C07D 471/04; C12N 5/0622; C12N 5/0602; C12N 2506/30; C12N 2501/999; A61K 45/06; A61K 31/437
See application file for complete search history.

(56) References Cited

U.S. PATENT DOCUMENTS

2010/0022580 A1   1/2010   Hung et al.

OTHER PUBLICATIONS

Mor, M., "Synthesis, pharmacological characterization and QSAR studies on 2-substituted indole melatonin receptor ligands." Bioorganic & medicinal chemistry 9.4 (2001): 1045-1057.*

Srinivasan, M., "Significance of NF-κB as a pivotal therapeutic target in the neurodegenerative pathologies of Alzheimer's disease and multiple sclerosis." Expert opinion on therapeutic targets 19.4 (2015): 471-487.*
International Search Report and Written Opinion issued by the ISA/US for PCT/US2015/033178 dated Nov. 12, 2015.
Barbieri and Ferlin, "Microwave-assisted one-pot synthesis of substituted tetrahydrocarbazole and 8,9,10,11-tetrahydro-7H-pyrido[a]carbazoles," Tetrahedron Letters, Nov. 2006, 47: 8289-8292.
Coldham et al., "Intramolecular Dipolar Cycloaddition Reactions to Give Substituted Indoles—A Formal Synthesis of Deethylibophyllidine," Eur. J Org. Chem., Jun. 2007, 2676-2686.
Fukuda et al., "Directed C-7 lithiation of 1-(2,2-diethylbutanoyl)indoles," Tetrahedron, Jul. 1999, 55: 9151-9162.
Gribble, "Recent developments in indole ring synthesis—methodology and applications," Contemp. Org. Synth, 1994, 1: 145-172.
He et al., "The Transcription Factor Yin Yang 1 is Essential for Oligodendrocyte Progenitor Differentiation," Neuron, 2007, 55: 217-30.
Lee et al., "Discovery of Ecopladib, an Indole Inhibitor of Cytosolic Phospholipase A2α," J Med. Chem., 2007, 50: 1380-1400.
Li and Vince, "Conformationally restrained carbazolone-containing α,γ-diketo acids as inhibitors of HIV integrase," Bioorg. & Med. Chem., May 2006, 14: 2942-2955.
Manzo et al., "Histone acetyltransferase inhibitors and preclinical studies," Expert Opin Ther Pat. 2009, (6):761-74.
Matsushima and Morell, "The Neurotoxicant, Cuprizone, as a Model to Study Demyelination and Remyelination in the Central Nervous System," Brain Pathol, Jan. 2001, 11: 107-116.
Miyabayashi et al., "Wnt/beta-catenin/CBP signaling maintains long-term murine embryonic stem cell pluripotency," PNAS, Mar. 2007, 104: 5668-73.
Miyamoto et al., "Total synthesis of (±)—debromoflustramine B and E and (±)—debromoflustramide B based on one-pot intramolecular Ullmann coupling and Claisen rearrangement," Tetrahedron Letters, Mar. 2007, 48: 1805-1808.
Mujtaba et al., "Structural Mechanism of the Bromodomain of the Coactivator CBP in p53 Transcriptional Activation," Mol Cell, Jan. 2004, 13: 251-263.
Rodriguez and Temprano, "Synthesis of 4-(N,N Dimethylaminoethyl)-1, 2, 3, 4-(3H)-one and Derivatives," J Chem. Soc. Perkins Trans. I, 1989, 2117-2122.
Shen et al., "Age-dependent epigenetic control of differentiation inhibitors is critical for remyelination efficiency," Nat Neurosci, Sep. 2008, 11: 1024-1034.
Teo et al., "Specific inhibition of CBP/β-catenin interaction rescues defects in neuronal differentiation caused by a presenilin-1 mutation," PNAS, Aug. 2005, 102: 12171-12176.
Extended European Search Report issued in European Application No. 15800337, dated Dec. 21, 2017, 10 pages.

(Continued)

*Primary Examiner* — John M Mauro
(74) *Attorney, Agent, or Firm* — Fish & Richardson P.C.

(57) ABSTRACT

This disclosure relates generally to compounds and compositions comprising one or more indole analogs. These compounds are useful for treating diseases associated with NF-kB and p53 activity, such as cancer and inflammatory diseases.

10 Claims, 17 Drawing Sheets

Specification includes a Sequence Listing.

(56) References Cited

OTHER PUBLICATIONS

Mor et al. "Synthesis, pharmacological characterization and QSAR studies on 2-substituted indole melatonin receptor ligands," Bioorganic & Medical Chemistry Pergamon, GB, vol. 9(4) Apr. 1, 2001, 14 pages.

Sachchidanand et al. "Target Structure-Based Discover of Small Molecules that Block Human P53 and CREB Binding Protein Association", Chemistry and Biology, vol. 13(1) Jan. 1, 2006, 10 pages.

* cited by examiner

FIG. 11

SMALL MOLECULE TRANSCRIPTION MODULATORS OF BROMODOMAINS

CROSS REFERENCE TO RELATED APPLICATION

This application claims priority to U.S. Provisional Application No. 62/005,645, filed May 30, 2014, the contents of which are hereby incorporated by reference in their entirety.

GOVERNMENT CLAUSE

This invention was made with government support under R01HG004508-03 awarded by The National Institutes of Health. The government has certain rights in the invention.

TECHNICAL FIELD

This disclosure relates generally to compounds and compositions comprising one or more indole analogs. These compounds are useful for treating diseases associated with NF-kB and p53 activity, such as cancer and inflammatory diseases.

BACKGROUND

Lysine acetylation mediates protein interactions in gene transcription. It is modulated by specific bromodomains (BRDs), which bind acetyl-lysine and are found in transcriptional co-activators with histone acetyltransferase activity such as CBP (CREB-binding protein) and chromatin-associating proteins. Bromodomain/acetyl-lysine binding is important for CBP acetyltransferase activity on biological targets, and for the recruitment of transcriptional proteins and enzymes affecting histone acetylation during gene activation. Previous studies have shown that lineage progression of progenitors towards myelinating oligodendrocytes is correlated with increased chromatin compaction and histone deacetylation. Oligodendrocytes are glial cells in the central nervous system, whose membrane forms the insulating coating termed myelin that wraps the axons and allows fast axonal conduction. Improper progenitor differentiation or myelin formation is detected in various neurological disorders.

In addition, transcriptional co-activators CREB-binding protein (CBP) and p300 (also known as KAT3B and KAT3A, respectively) play a central role in regulating p53 stability and its function as a transcription factor in response to genotoxic stress. Like histones, lysine acetylation of transcription factors facilitates the recruitment of BRD-containing cofactors required for chromatin structural change and transcriptional initiation and elongation. The biochemical contribution of acetylation to p53 transcription functions has been attributed to nuclear translocation, alteration of DNA binding ability and enhancement of transcriptional potential. p53 acetylation plays an important part in promoting molecular interactions with transcriptional co-regulators leading to target gene activation that ultimately determines cellular responses to stress in the forms of senescence, cell growth arrest, or apoptosis.

SUMMARY

Provided herein is a compound of formula (1):

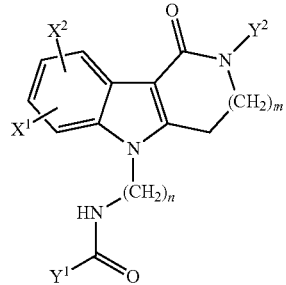

or a pharmaceutically acceptable salt form thereof, wherein:

$Y^1$ is selected from the group consisting of: H, $C_1$-$C_6$ alkyl, $C_1$-$C_6$ haloalkyl, halo, and —$OR^3$;

$Y^2$ is selected from the group consisting of H, $C_1$-$C_6$ alkyl, $C_1$-$C_6$ haloalkyl, halo, and —$OR^3$, or $Y^2$ can form a fused cyclic ring system;

$X^1$ and $X^2$ are independently selected from the group consisting of: H, $C_1$-$C_6$ alkyl, $C_1$-$C_6$ haloalkyl, halo, —$NO_2$, —OH, —O($C_1$-$C_6$ alkyl), —O($C_1$-$C_6$ haloalkyl), —S($C_1$-$C_6$ alkyl), —$NR^1R^2$, —$NR^1(C(O)R^2)$, —C(O)($C_1$-$C_6$ alkyl), —C(O)$OR^1$, —C(O)$NR^1R^2$, $C_5$-$C_{14}$ aryl, and $C_4$-$C_{14}$ heteroaryl;

each $R^1$ and $R^2$ are independently selected from H and $C_1$-$C_6$ alkyl;

each $R^3$ is independently selected from H, $C_1$-$C_6$ alkyl, and $C_5$-$C_{14}$ aryl;

n and m are independently integers from 1 to 6.

In some embodiments, $Y^1$ is —$OR^3$. For example, $Y^1$ can be —OH or —OPh. In some embodiments, $Y^1$ is a $C_1$-$C_6$ alkyl. For example, $Y^1$ is $CH_3$ or $CH_2CH_3$.

In some embodiments, $Y^2$ is selected from the group consisting of H, $C_1$-$C_6$ alkyl, and —$OR^3$. In some embodiments, $Y^2$ forms a fused cyclic ring system selected from the group consisting of: $C_3$-$C_{12}$ cycloalkyl, $C_3$-$C_{12}$ heterocycloalkyl, $C_4$-$C_{14}$ aryl, and $C_3$-$C_{14}$ heteroaryl. For example, $Y^2$ is a fused imidazolyl or a fused pyrrolyl. In some embodiments, $Y^2$ is H.

In some embodiments, $X^1$ and $X^2$ are H.

Non-limiting examples of a compound of formula (1) include:

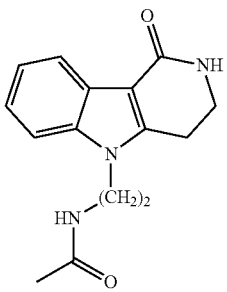 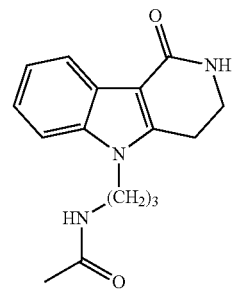

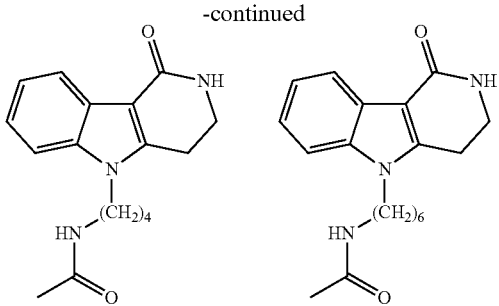

or a pharmaceutically acceptable salt form thereof.

Also provided herein is a compound of formula (2):

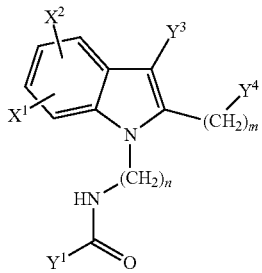

or a pharmaceutically acceptable salt form thereof,
wherein:
$Y^1$ is selected from the group consisting of: H, $C_1$-$C_6$ alkyl, $C_1$-$C_6$ haloalkyl, halo, and —$OR^3$;
$Y^3$ and $Y^4$ are independently selected from the group consisting of H, $C_1$-$C_6$ alkyl, $C_1$-$C_6$ haloalkyl, halo, —$NO_2$, —OH, —O($C_1$-$C_6$ alkyl), —($C_5$-$C_{14}$ aryl), —O($C_1$-$C_6$ haloalkyl), —S($C_1$-$C_6$ alkyl), —$NR^1R^2$, —$NR^1(C(O)R^2)$, —C(O)($C_1$-$C_6$ alkyl), —C(O)$OR^1$, —C(O)$NR^1R^2$, $C_5$-$C_{14}$ aryl, and $C_4$-$C_{14}$ heteroaryl, or $Y^3$ and $Y^4$ can come together to form a cyclic ring system;
$X^1$ and $X^2$ are independently selected from the group consisting of: H, $C_1$-$C_6$ alkyl, $C_1$-$C_6$ haloalkyl, halo, —$NO_2$, —OH, —O($C_1$-$C_6$ alkyl), —O($C_1$-$C_6$ haloalkyl), —S($C_1$-$C_6$ alkyl), —$NR^1R^2$, —$NR^1(C(O)R^2)$, —C(O)($C_1$-$C_6$ alkyl), —C(O)$OR^1$, —C(O)$NR^1R^2$, $C_5$-$C_{14}$ aryl, and $C_4$-$C_{14}$ heteroaryl;
each $R^1$ and $R^2$ are independently selected from H and $C_1$-$C_6$ alkyl;
$R^3$ is independently selected from H and $C_5$-$C_{14}$ aryl;
n and m are independently integers from 1 to 6.

In some embodiments, $Y^1$ is —$OR^3$. For example, $Y^1$ can be —OH or —OPh. In some embodiments, $Y^1$ is a $C_1$-$C_6$ alkyl. For example, $Y^1$ can be $CH_3$ or $CH_2CH_3$.

In some embodiments, $Y^3$ and $Y^4$ come together to form a cyclic ring system selected from the group consisting of: $C_3$-$C_{12}$ cycloalkyl, $C_3$-$C_{12}$ heterocylcloalkyl, $C_4$-$C_{14}$ aryl, and $C_3$-$C_{14}$ heteroaryl. For example, the cyclic ring system can be selected from imidazolyl and pyrrolyl.

This disclosure also provides for a pharmaceutical composition comprising a compound of formula (1) or formula (2), or a pharmaceutically acceptable salt thereof, and a pharmaceutically acceptable excipient.

The compounds described herein can be used, for example, to promote neural repair in a patient, the method comprising administering a therapeutically effective amount of a compound of formula (1) or formula (2), or a pharmaceutically acceptable salt form thereof, to the patient. Neural repair can be promoted, for example, through the promotion of the lineage progression of oligodendrocyte progenitors toward a differentiated state. In some embodiments, the lysine acetylation of histones, transcription regulator proteins, transcriptional co-activators, or other chromatin-associated proteins by bromodomain containing histone acetyltransferase (HAT) transcriptional co-activators are inhibited.

Also provided herein is a method of treating a neurodegenerative autoimmune disease is a patient, the method comprising administering a therapeutically effective amount of a compound of formula (1) or formula (2), or a pharmaceutically acceptable salt form thereof, to the patient. The neurodengenerative autoimmune disease can be selected from the group consisting of: multiple sclerosis, acute disseminated encephalomyelitis, transverse myelitis, chronic inflammatory demyelinating polyneuropathy, Guillain-Barré syndrome, central pontine myelinosis, and inherited demyelinating diseases.

Further provided herein is a method of promoting lineage progression of adult stem cells, the method comprising contacting the cells with a therapeutically effective amount of a compound of formula (1) or formula (2), or a pharmaceutically acceptable salt form thereof. In some embodiments, the cells are oligodendrocyte progenitor cells.

A method for treating a demyelinating disorder in a patient is provided herein, the method comprising administering a therapeutically effective amount of a compound of formula (1) or formula (2), or a pharmaceutically acceptable salt form thereof, to the patient. For example, administration of a compound of formula (1) or formula (2) can increase myelination of a neuron in the patient.

In some embodiments, administration of a compound of formula (1) or formula (2) can be useful for treating a disease or disorder in a patient, the method comprising administering to the patient a therapeutically effective amount of a compound that inhibits the acetyl-lysine binding activity of a bromodomain containing transcriptional co-activator, transcription regulator protein, or chromatin remodeling regulator protein. The disease or disorder can include HIV/AIDS, cancer, inflammatory disease, auto-immune disease, cardiovascular disease, neurological disorders, metabolic disorders, a disease or condition wherein p53 is hyper-activated under a stress-induced event, circadian rhythm disorders, drug addiction, and neurodegenerative auto-immune disease.

In some embodiments, the inhibition of binding activity attenuates the gene transcriptional activity of the transcriptional co-activator, transcription regulator protein, or chromatin remodeling regulator protein. In some embodiments, the compound forms hydrogen bond contacts with an acetyl-lysine binding asparagine residue of the bromodomain containing transcriptional co-activator, transcription regulator protein, or chromatin remodeling regulator protein.

A transcriptional co-activator, transcription regulator protein, or chromatin remodeling regulator protein can include: PCAF, GCN5L2, p300, CBP, TAF1, TAF1L, Ash1L, MLL, SMARCA2, SMARCA4, BRPF1, ATAD2, BRD7, BRD2, BRD3, BRD4, BRDT, BAZ1B (WSTF), BAZ2B, BPTF, SP140L, TRIM24, and TRIM33.

Also provided herein is a method for modulating gene transcription in a patient. The method can include administering to the patient a therapeutically effective amount of a compound of formula (1) or formula (2), or a pharmaceutically acceptable salt form thereof. In some embodiments, gene transcription is modulated by inhibiting recruitment of bromodomain containing transcriptional co-activators, transcription regulator proteins, or chromatin remodeling regulator proteins to chromatin; inhibiting lysine acetylation of histones, transcription regulator proteins, transcriptional co-activators, or other chromatin-associated proteins by bromodomain containing histone acetyltransferase (HAT) transcriptional co-activators; and/or inhibiting interactions between bromodomain containing transcriptional co-activators, transcription regulator proteins, chromatin remodeling regulator proteins, and other chromatin-associated proteins in complexes that are required for gene transcription In some embodiments, modulation occurs in one or more of the NF-kB, IL6, and p53 pathways. In some embodiments, the transcriptional co-activator, transcription regulator protein, or chromatin remodeling regulator protein is selected from the group selected from: PCAF, GCN5L2, p300/CBP, TAF1, TAF1L, Ash1L, MLL, SMARCA2, SMARCA4, BRPF1, ATAD2, BRD7, BRD2, BRD3, BRD4, BRDT, BAZ1B (WSTF), BAZ2B, BPTF, SP140L, TRIM24, TRIM33, or a combination thereof.

The method can further include administrating a therapeutically effective amount of a histone acetyltransferase inhibitor to the patient.

A number of diseases and disorders in a patient can be treated and/or ameliorated through administration of a therapeutically effective amount of a compound of formula (1) or formula (2), or a pharmaceutically acceptable salt form thereof. In some embodiments, the disease or disorder is one where NF-kB is implicated in the pathology of the disorder.

For example, HIV/AIDS can be treated in a patient. In some embodiments, the compound modulates PCAF transcriptional activity.

In some embodiments, the disease occurs when NF-kB is over activated. For example, cancer, inflammatory disease, auto-immune disease, cardiovascular disease, neurological disorders, and metabolic disorders (e.g., type 2 diabetes mellitus).

Non-limiting examples of cancer include B cell lymphoma, Hodgkin's disease, T cell lymphoma, adult T cell lymphoma, adult T cell leukemia, acute lymphoblastic leukemia, breast cancer, liver cancer, thyroid cancer, pancreatic cancer, prostate cancer, melanoma, head and neck SCC, colon cancer, multiple myeloma, ovarian cancer, bladder cancer, lung carcinoma.

Non-limiting examples of inflammatory disease include rheumatoid arthritis, inflammatory bowel disease, multiple sclerosis, type 1 diabetes, lupus, asthma, psoriasis, sepsis, gastritis, and post ischemic inflammation (e.g., stroke and myocardial infarction).

A neurological disorder can include Alzheimer's disease and Parkinson's disease.

In some embodiments, administration of a therapeutically effective amount of a compound of formula (1) or formula (2), or a pharmaceutically acceptable salt thereof, can modulate transcriptional activity of NF-kB and its target genes in a patient.

In some embodiments, the disease or disorder is a retroviral infection or myocardial hypertrophy.

Also provided herein is a method of inducing stem cell differentiation in a patient, the method comprising administering a therapeutically effective amount of a compound of formula (1) or formula (2), or a pharmaceutically acceptable salt form thereof, to the patient. In some embodiments, the stem cells are cancer stem cells.

A method of inducing apoptosis of malignant cells in a patient is provided. The method comprising administering a therapeutically effective amount of a compound of formula (1) or formula (2), or a pharmaceutically acceptable salt form thereof, to the patient.

In some embodiments, P-TEFb is regulated in a patient through administration of a therapeutically effective amount of a compound of formula (1) or formula (2), or a pharmaceutically acceptable salt form thereof, to the patient. For example, P-TEFb can be regulated by binding the bromodomains of BRD4.

Further provided herein is a method for modulating the transcriptional activity of human p53 and activation of its target genes in a patient, the method comprising administering a therapeutically effective amount of a compound of formula (1) or formula (2), or a pharmaceutically acceptable salt form thereof, to the patient. In some embodiments, the modulating is down-regulating. For example, down-regulating of p53 transcription activity enhances the reprogramming efficiency of induced pluripotent stem cells using one or more stem cell factors selected from Oct3/4, Sox2, Klf4, and c-Myc. In some embodiments, the modulating is useful in the treatment of disease or condition wherein p53 activity is hyper-activated under a stress-induced event. For example, a stress-induced event such as trauma, hyperthermia, hypoxia, ischemia, stroke, a burn, a seizure, a tissue or organ prior to transplantation, and a chemo- or radiation therapy treatment.

The compounds described herein can also be useful for modulating the transcriptional activity of transcription co-activators CBP/p300 by binding to the bromodomain in a patient, the method comprising administering a therapeutically effective amount of a compound of formula (1) or formula (2), or a pharmaceutically acceptable salt form thereof, to the patient. In some embodiments, CBP/p300 activity is associated with inducing or promoting a disease or condition selected from the group consisting of: cancer, acute myeloid leukemia (AML), chronic myeloid leukemia, circadian rhythm disorders, and drug addiction.

Further provided herein is a method for modulating the transcriptional activity of Williams-Beuren syndrome transcription factor (WSTF) by binding to the bromodomain in a patient, the method comprising administering a therapeutically effective amount of a compound of formula (1) or formula (2), or a pharmaceutically acceptable salt form thereof, to the patient. In some embodiments, the WSTF hyper-activity modulated occurs in an over-expressed vitamin A receptor complex in one or more of a cancer of the breast, head and neck, and lungs, leukemia, and skin cancers.

In some embodiments, the methods described herein can further include administering a therapeutically effective amount of an anticancer agent to the patient. For example, irinotecan, daunorubicin, doxorubicin, vinblastine, vincristine, etoposide, actinmycin D, cisplatin, paclitaxel, gemcitabine, SAHA, and combinations thereof. In some embodiments, the patient is resistant to one or more cytotoxic chemotherapeutic agents.

In some embodiments, the methods provided herein also include administrating a therapeutically effective amount of a histone acetyltransferase inhibitor to the patient.

The methods described herein may also be conducted in vitro (for example, in a cell) by contacting a cell with a therapeutically effective amount of a compound of formula (1) or formula (2), or a pharmaceutically acceptable salt form thereof. For example, modulating gene transcription in a cell; modulating the transcriptional activity of PCAF in HIV transcriptional activity and replication in a cell; inhibiting transcriptional activity of NF-kB in a cell; inducing stem cell differentiation; inducing apoptosis of a malignant cell; regulating P-TEFb in a cell; modulating the transcriptional activity of human p53 and activation of its target genes in a cell; modulating the transcriptional activity of transcription co-activators CBP/p300 by binding to the bromodomain in a cell; modulating the transcriptional activity of Williams-Beuren syndrome transcription factor (WSTF) by binding to the bromodomain in a cell; and modulating transcriptional activity of PCAF in a cell The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 11 shows the sequence alignment of individual human BRDs. Sequence numbers for the corresponding proteins are shown before and after the sequences (CREBBP (SEQ ID NO:1, EP300 (SEQ ID N0:2, BRD2_D1 (SEQ ID NO:3, BRD3_D1 (SEQ ID NO:4, BRD4_D1 (SEQ IDNO: 5), BRDT_D1 (SEQ ID NO:6), BRD2_D2 (SEQ ID NO:7), BRD3_D2 (SEQ ID NO:8), BRD4_D2 (SEQ ID NO:9), ATAD2 (SEQ ID NO:10), ATAD2B (SEQ ID NO:11), BRD7 (SEQ ID NO:12), BRD9 (SEQ ID NO:13), BRPF1 (SEQ ID NO:14), TRIM24 (SEQ ID NO:15), TRIM28 (SEQ ID NO:16), BAZ2B (SEQ ID NO:17), GCN5L2 (SEQ ID NO:18), PCAF (SEQ ID NO:19), BPTF (SEQ ID NO:20), TAF1_D2 (SEQ ID NO:21), TAF1L_D2 (SEQ ID NO:22), TAF1_D1 (SEQ ID NO:23), SMARCA4 (SEQ ID NO:24), SMARCA2 (SEQ ID NO:25), PBRM1_D5 (SEQ ID NO:26), PBRM1_D2 (SEQ ID NO:27), PBRM1_D1 (SEQ ID NO:28), PBRM1_D3 (SEQ ID NO:29), PBRM1_D6 (SEQ ID NO:30) Highly conserved residues in the BRDs are highlighted in bold.

DETAILED DESCRIPTION

Definitions

Figure 1:
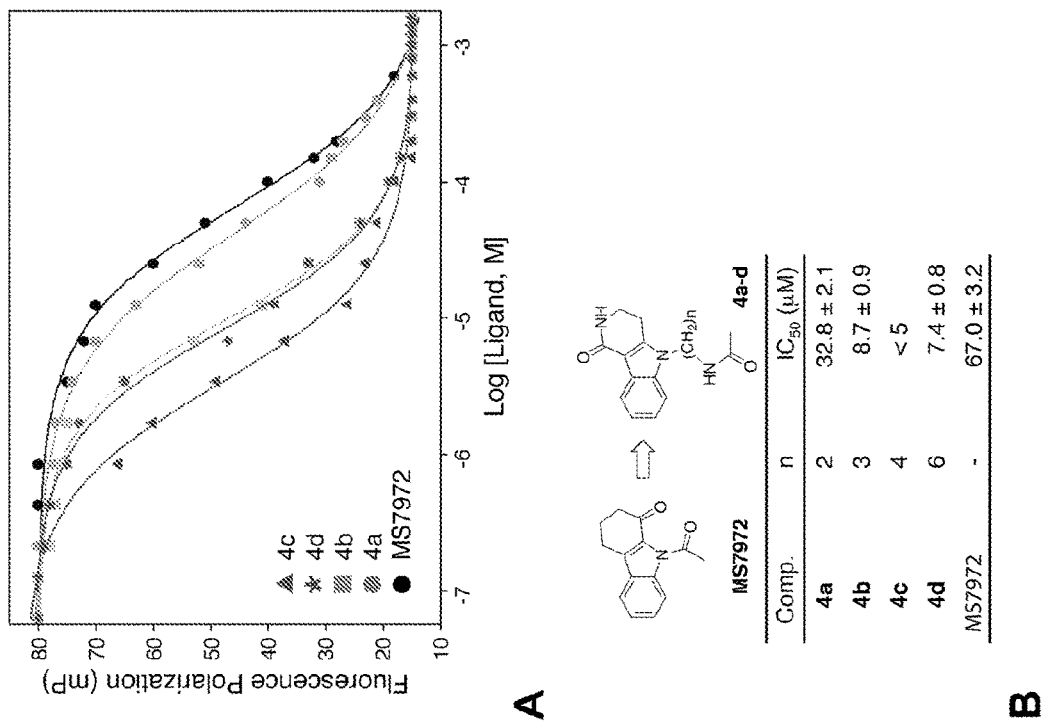
FIG. 1A is a line drawing of the florescence polarization competition assay measuring the binding affinity of compounds 4a-d to the CBP BRD.
FIG. 1B provides the $IC_{50}$ values of compounds 4a-d and MS7972. Results are representative of three independent experiments and the error is SD.

Unless defined otherwise, all technical and scientific terms used herein have the same meaning as is commonly understood by one of ordinary skill in the art to which this disclosure belongs. All patents, applications, published applications, and other publications cited herein are incorporated by reference in their entirety. In the event that there is a plurality of definitions for terms cited herein, those in this section prevail unless otherwise stated.

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about", whether or not the term is explicitly used, unless explicitly stated otherwise. As used herein, the singular forms "a," "an," and "the" include plural referents unless the context clearly dictates otherwise.

A "patient," as used herein, includes both humans and other animals, particularly mammals. Thus the methods are applicable to both human therapy and veterinary applications. In some embodiments, the patient is a mammal, for example, a primate. In some embodiments, the patient is a human.

The terms "treating" and "treatment" mean causing a therapeutically beneficial effect, such as ameliorating existing symptoms, preventing additional symptoms, ameliorating or preventing the underlying metabolic causes of symptoms, postponing or preventing the further development of a disorder and/or reducing the severity of symptoms that will or are expected to develop.

A "therapeutically effective" amount of the compounds described herein is typically one which is sufficient to achieve the desired effect and may vary according to the nature and severity of the disease condition, and the potency of the compound. It will be appreciated that different concentrations may be employed for prophylaxis than for treatment of an active disease.

The term "contacting" means bringing at least two moieties together, whether in an in vitro system or an in vivo system.

As used herein, "modulating transcriptional activity" refers to both down-regulation and up-regulation of a set of genes in a pathway. For example, inhibition of a transcription factor expression could result in down-regulation of a set of genes that this transcription factor directly targets to activate, while also resulting in the up-regulation of another set of genes that this transcription factor's target genes function to repress.

The term "bioisostere" means a substituent that is believed to impart similar biological properties to a compound as an identified substituent. Accordingly, a bioisostere of phenol, as used herein, refers to a substituent that is believed to impart similar biological properties as a phenol moiety to the compounds described herein.

In general, reference to a certain element such as hydrogen or H is meant to include all isotopes of that element. For example if a R group is defined to represent hydrogen or H, it also includes deuterium and tritium.

The term "alkyl" includes straight-chain alkyl groups (e.g., methyl, ethyl, propyl, butyl, pentyl, hexyl, heptyl, octyl, nonyl, decyl, etc.) and branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. In certain embodiments, a straight chain or branched chain alkyl has 6 or fewer carbon atoms in its backbone (e.g., $C_{1-60}$ for straight chain, $C_{3-10}$ for branched chain). The term $C_{1-6}$ includes alkyl groups containing 1 to 6 carbon atoms.

The term "cycloalkyl" includes a cyclic aliphatic group which may be saturated or unsaturated. For example, cycloalkyl groups include cyclopropyl, cyclopentyl, cyclohexyl, cycloheptyl, and cyclooctyl. In some embodiments, cycloalkyls have from 3-8 carbon atoms in their ring structure, for example, they can have 3, 4, 5 or 6 carbons in the ring structure.

In general, the term "aryl" includes groups, including 5- and 6-membered single-ring aromatic groups, such as benzene and phenyl. Furthermore, the term "aryl" includes multicyclic aryl groups, e.g., tricyclic, bicyclic, such as naphthalene and anthracene.

The term "heteroaryl" includes groups, including 5- and 6-membered single-ring aromatic groups, that have from one to four heteroatoms, for example, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "heteroaryl" includes multicyclic heteroaryl groups, e.g., tricyclic, bicyclic, such as benzoxazole, benzodioxazole, benzothiazole, benzoimidazole, benzothiophene, methylenedioxyphenyl, quinoline, isoquinoline, napthyridine, indole, benzofuran, purine, benzofuran, quinazoline, deazapurine, indazole, or indolizine.

The term "heterocycloalkyl" includes groups, including but not limited to, 3- to 10-membered single or multiple rings having one to five heteroatoms, for example, piperazine, pyrrolidine, piperidine, or homopiperazine.

The term "substituted" means that an atom or group of atoms formally replaces hydrogen as a "substituent" attached to another group. For aryl and heteroaryl groups, the term "substituted", unless otherwise indicated, refers to any level of substitution, namely mono, di, tri, tetra, or penta substitution, where such substitution is permitted. The substituents are independently selected, and substitution may be at any chemically accessible position. In some cases two sites of substitution may come together to form a 3-10 membered cycloalkyl or heterocycloalkyl ring.

As used herein, "administration" refers to delivery of a compound or composition as described herein by any external route, including, without limitation, IV, intramuscular, SC, intranasal, inhalation, transdermal, oral, buccal, rectal, sublingual, and parenteral administration.

Compounds

Provided herein are compounds of formula (1):

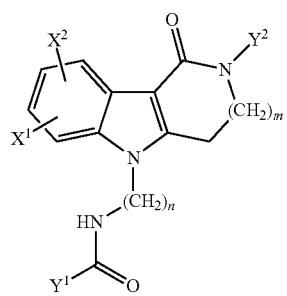

or a pharmaceutically acceptable salt form thereof, wherein:

$Y^1$ is selected from the group consisting of: H, $C_1$-$C_6$ alkyl, $C_1$-$C_6$ haloalkyl, halo, and a heteroatom containing group that is capable of accepting or donating a hydrogen bond or establishing electrostatic or Van der Waals interactions with a target protein;

$Y^2$ is selected from the group consisting of H, $C_1$-$C_6$ alkyl, $C_1$-$C_6$ haloalkyl, halo, and a heteroatom containing group that is capable of accepting or donating a hydrogen bond or establishing electrostatic or Van der Waals interactions with a target protein, or $Y^2$ can form a fused cyclic ring system;

$X^1$ and $X^2$ are independently selected from the group consisting of: H, $C_1$-$C_6$ alkyl, $C_1$-$C_6$ haloalkyl, halo, —$NO_2$, —OH, —O($C_1$-$C_6$ alkyl), —O($C_1$-$C_6$ haloalkyl), —S($C_1$-$C_6$ alkyl), —$NR^1R^2$, —$NR^1$(C(O)$R^2$), —C(O)($C_1$-$C_6$ alkyl), —C(O)O$R^1$, —C(O)$NR^1R^2$, $C_5$-$C_{14}$ aryl, and $C_4$-$C_{14}$ heteroaryl;

each $R^1$ and $R^2$ are independently selected from H and $C_1$-$C_6$ alkyl; and n and m are independently integers from 1 to 6.

A heteroatom containing group that is capable of accepting or donating a hydrogen bond or establishing electrostatic or Van der Waals interactions with a target protein can include, for example, —$OR^3$, wherein each $R^3$ is independently selected from H, $C_1$-$C_6$ alkyl, and $C_5$-$C_{14}$ aryl. For example, —$OR^3$ can be —OH, —OPh, or a bioisotere of phenol.

In some embodiments, $Y^1$ is —$OR^3$. For example $Y^1$ is —OH or —OPh. In some embodiments, $Y^1$ is a $C_1$-$C_6$ alkyl. For example, $Y^1$ is $CH_3$ or $CH_2CH_3$.

In some embodiments, $Y^2$ is selected from the group consisting of H, $C_1$-$C_6$ alkyl, and —$OR^3$ (e.g., —OH or —OPh). In some embodiments, $Y^2$ forms a fused cyclic ring system selected from the group consisting of: $C_3$-$C_{12}$ cycloalkyl, $C_3$-$C_{12}$ heterocylcloalkyl, $C_4$-$C_{14}$ aryl, and $C_3$-$C_{14}$ heteroaryl. For example, $Y^2$ is a fused imidazolyl or a fused pyrrolyl. In some embodiments, $Y^2$ is H.

In some embodiments, $X^1$ and $X^2$ are H.

Non-limiting examples of a compound of formula (1) include:

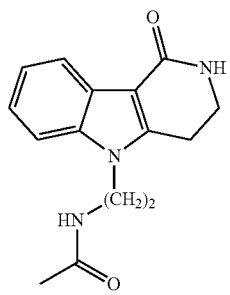 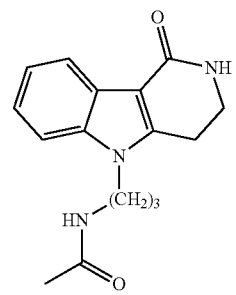

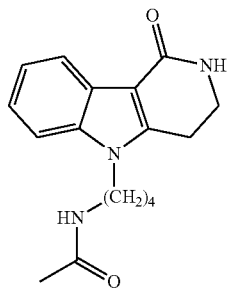 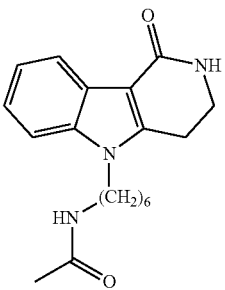

or a pharmaceutically acceptable salt form thereof.

Also provided herein are compounds of formula (2):

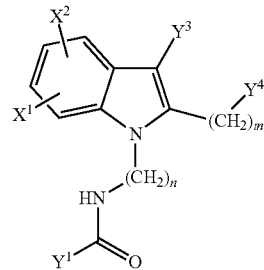

or a pharmaceutically acceptable salt form thereof, wherein:

$Y^1$ is selected from the group consisting of: H, $C_1$-$C_6$ alkyl, $C_1$-$C_6$ haloalkyl, halo, and a heteroatom containing group that is capable of accepting or donating a hydrogen bond or establishing electrostatic or Van der Waals interactions with a target protein;

$Y^3$ and $Y^4$ are independently selected from the group consisting of H, $C_1$-$C_6$ alkyl, $C_1$-$C_6$ haloalkyl, halo, —$NO_2$, —OH, —O($C_1$-$C_6$ alkyl), —O($C_5$-$C_{14}$ aryl), —O($C_1$-$C_6$ haloalkyl), —S($C_1$-$C_6$ alkyl), —$NR^1R^2$, —$NR^1$(C(O)$R^2$), —C(O)($C_1$-$C_6$ alkyl), —C(O)O$R^1$, —C(O)$NR^1R^2$, $C_5$-$C_{14}$ aryl, $C_4$-$C_{14}$ heteroaryl, and a heteroatom containing group that is capable of accepting or donating a hydrogen bond or establishing electrostatic or Van der Waals interactions with a target protein, or $Y^3$ and $Y^4$ can come together to form a cyclic ring system;

$X^1$ and $X^2$ are independently selected from the group consisting of: H, $C_1$-$C_6$ alkyl, $C_1$-$C_6$ haloalkyl, halo, —$NO_2$, —OH, —O($C_1$-$C_6$ alkyl), —O($C_1$-$C_6$ haloalkyl), —S($C_1$-$C_6$ alkyl), —$NR^1R^2$, —$NR^1$(C(O)$R^2$), —C(O)($C_1$-$C_6$ alkyl), —C(O)O$R^1$, —C(O)$NR^1R^2$, $C_5$-$C_{14}$ aryl, and $C_4$-$C_{14}$ heteroaryl;

each $R^1$ and $R^2$ are independently selected from H and $C_1$-$C_6$ alkyl; and n and m are independently integers from 1 to 6.

A heteroatom containing group that is capable of accepting or donating a hydrogen bond or establishing electrostatic or Van der Waals interactions with a target protein can include, for example, —$OR^3$, wherein $R^3$ is independently selected from H and $C_5$-$C_{14}$ aryl. For example, —$OR^3$ can be —OH, —OPh, or a bioisotere of phenol.

In some embodiments, $Y^1$ is —$OR^3$. For example, $Y^1$ is —OH or —OPh. In some embodiments, $Y^1$ is a $C_1$-$C_6$ alkyl. For example, $Y^1$ is $CH_3$ or $CH_2CH_3$.

In some embodiments, $Y^3$ and $Y^4$ come together to form a cyclic ring system selected from the group consisting of: $C_3$-$C_{12}$ cycloalkyl, $C_3$-$C_{12}$ heterocylcloalkyl, $C_4$-$C_{14}$ aryl, and $C_3$-$C_{14}$ heteroaryl. For example, the cyclic ring system can be selected from imidazolyl and pyrrolyl.

Further provided herein is a compound 4e:

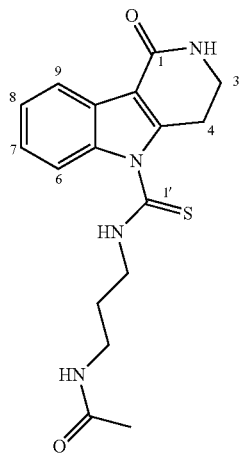 [SMILES: CC(=O)NCCCNC(=S)n1c2c(c3ccccc31)C(=O)NCC2]

or a pharmaceutically acceptable salt form thereof.

reaction can be carried out in one solvent or a mixture of more than one solvent. Depending on the particular reaction step, suitable solvents for a particular reaction step can be selected by the skilled artisan.

Preparation of compounds can involve the protection and deprotection of various chemical groups. The need for protection and deprotection, and the selection of appropriate protecting groups, can be readily determined by one skilled in the art. The chemistry of protecting groups can be found, for example, in *Protecting Group Chemistry*, 1st Ed., Oxford University Press, 2000; and *March's Advanced Organic chemistry: Reactions, Mechanisms, and Structure*, 5th Ed., Wiley-Interscience Publication, 2001 (each of which is incorporated herein by reference in their entirety).

A compound of formula (1) can be prepared, for example, as shown in Scheme 1.

Scheme 1.

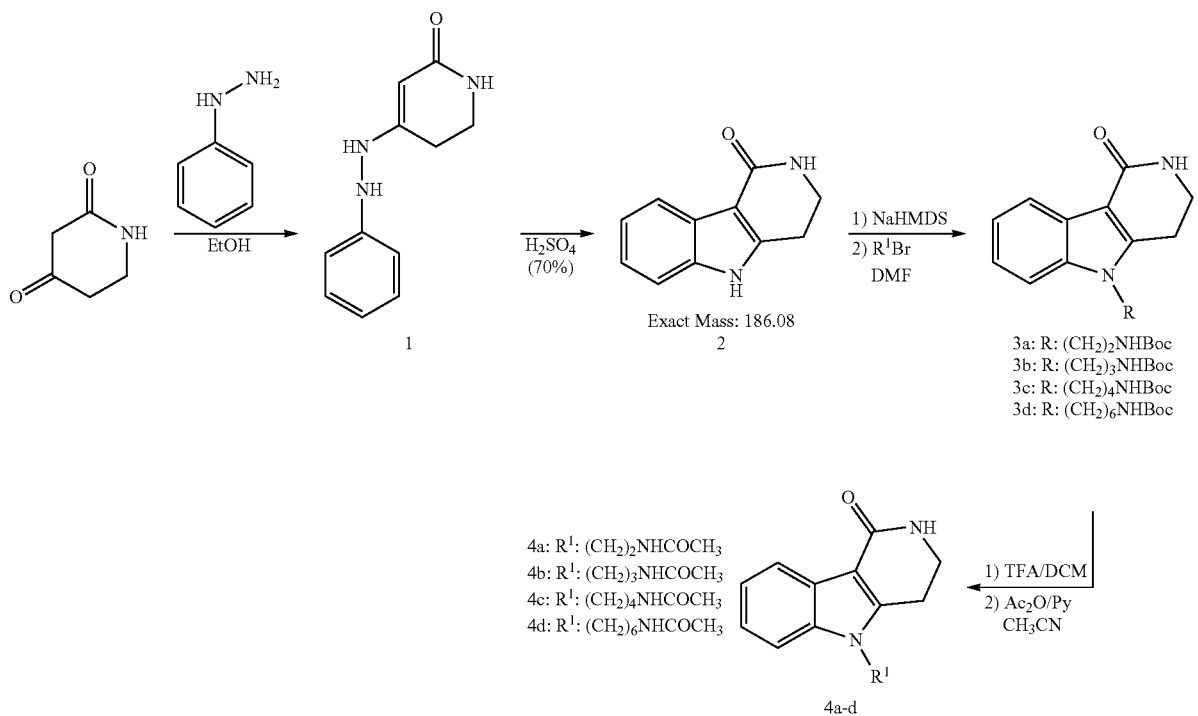

Compounds described herein, including pharmaceutically acceptable salts thereof, can be prepared using known organic synthesis techniques and can be synthesized according to any of numerous possible synthetic routes.

The reactions for preparing the compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given Briefly, compound 1 can be prepared by reaction of phenylhydrazine with commercially available 2,4-piperidinedione in ethanol under nitrogen atmosphere. Next, the pyrido-indole scaffold is constructed following the Fisher indole synthesis, by treatment of phenylhydrazone 1 with sulfuric acid (70%). The 2,3,4,5-tetrahydro-1H-pyrido-[4,3-b]indol-1-one 2 can then be N-alkylated with the suitable tert-butoxycarbonyl-protected alkyl bromide, using lithium bis(trimethylsilyl) amide as a base. Other bases such as KOH, NaH or BuLi can also be used. Finally, treatment of N-tert-butoxycarbonyl substituted pyrido-indoles with trifluoroacetic acid and subsequent acetylation with acetyl chloride/propylene oxide afforded compounds 4a-d with good yields.

A compound of formula (2) can be prepared, for example, as shown in Scheme 2.

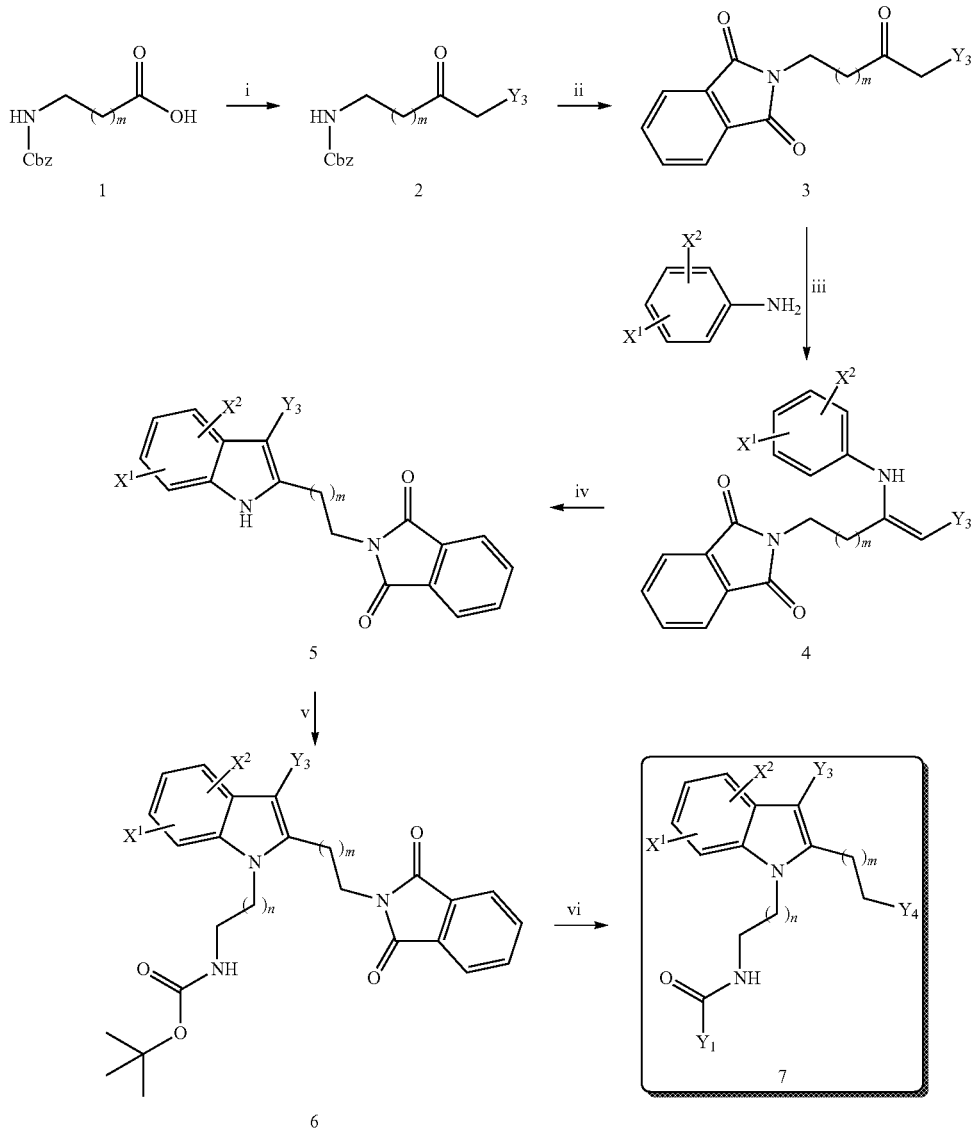

Scheme 2.

(i) Carbonyldiimidazol, KOCOCH$_2$Y$_3$, MgCl$_2$, THF. (ii) (a) Pd—C, H$_2$, MeOH, (b) Phthalic anhydride, hexamethyldiziloxane, ZnBr$_2$, THF (iii) Zn(ClO$_4$)$_2$ 6H$_2$O, MgSO$_4$, CH$_2$Cl$_2$ (iv) Pd(OAc)$_2$, Cu(OAc)$_2$, K$_2$CO$_3$, DMF, 90° C. (v) (a) NaHMDS, -78° C., DMF (b) Br(CH$_2$)$_n$NHBoc (vi) (a) TFA, TIS, CH$_2$Cl$_2$ (b) Y$_1$COCl, Propylene Oxide, CH$_3$CN (c) NH$_2$—NH$_2$, CH$_3$OH (e) RCOCl, Propylene Oxide, CH$_3$CN.

In some embodiments, starting from the cbz protected β-alanine 1, the β-ketoester 2 can be prepared. Next, the cbz protecting group in 2 can be replaced to form the more stable pthalimide 3, which is transformed into the corresponding β-enaminoester 4 by reaction with a substituted 2-iodoaniline in the presence of a catalytic amount of a lewis acid. The cyclization to furnish the indol scaffold (5) can be performed by using palladium and copper acetate as catalysts, and potassium carbonate as a base. Next, N-alkylation on the N-indol leads to the substituted heterocycle 6, which by means of deprotection/acetylation on the indole N-substituent and subsequent phthalimide deprotection/acylation on the C-2 aminoethyl group allows for the preparation of the target indole 7.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS) or thin layer chromatography (TLC). Compounds can be purified by those skilled in the art by a variety of methods, including high performance liquid chromatography (HPLC) ("*Preparative LC-MS Purification: Improved Compound Specific Method Optimization*" K. F. Blom, et al., *J. Combi. Chem.* 6(6) (2004), which is incorporated herein by reference in its entirety) and normal phase silica chromatography.

Pharmaceutically Acceptable Salts and Compositions

Pharmaceutically acceptable salts of the compounds described herein include the acid addition and base salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, hydrogen phosphate, isethionate, D- and L-lactate, malate, maleate, malonate, mesylate, methylsulphate, 2-napsylate, nicotinate, nitrate, orotate, oxalate, palmitate, pamoate, phosphate/hydrogen, phosphate/phosphate dihydrogen, pyroglutamate, saccharate, stearate, succinate, tannate, D- and L-tartrate, 1-hydroxy-2-naphthoate tosylate and xinafoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

Compounds described herein intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

The compounds may be administered alone or in combination with one or more other compounds described herein or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Non-limiting examples of pharmaceutical excipients suitable for administration of the compounds provided herein include any such carriers known to those skilled in the art to be suitable for the particular mode of administration. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β-, and γ-cyclodextrin, or chemically modified derivatives such as hydroxyalkylcyclodextrins, including 2- and 3-hydroxypropyl-b-cyclodextrins, or other solubilized derivatives can also be advantageously used to enhance delivery of compounds of the formulae described herein. In some embodiments, the excipient is a physiologically acceptable saline solution.

The compositions can be, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers (see, e.g., *Ansel Introduction to Pharmaceutical Dosage Forms, Fourth Edition* 1985, 126).

The concentration of a compound in a pharmaceutical composition will depend on absorption, inactivation and excretion rates of the compound, the physicochemical characteristics of the compound, the dosage schedule, and amount administered as well as other factors known to those of skill in the art.

The pharmaceutical composition may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal patients and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Dosage forms or compositions containing a compound as described herein in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

Pharmaceutical compositions suitable for the delivery of compounds described herein and methods for their preparation will be readily apparent to those skilled in the art. Such compositions and methods for their preparation may be found, for example, in *Remington's Pharmaceutical Sciences,* 19th Edition (Mack Publishing Company, 1995).

Methods of Use

The compounds and compositions provided herein can be used as a method of treating a disease or disorder in a patient by inhibiting the acetyl-lysine binding activity of a bromodomain containing transcriptional co-activator, transcription regulator protein, or chromatin remodeling regulator protein. Such inhibition can lead to attenuated gene transcriptional activity that induces or contributes to the disease or disorder. In some embodiments, a compound as described herein makes hydrogen bond contacts with an acetyl-lysine binding asparagine residue of a bromodomain containing transcriptional co-activator, transcription regulator protein, or chromatin remodeling regulator protein.

The transcriptional co-activator, transcription regulator protein, or chromatin remodeling regulator protein can include one or more of PCAF, GCN5L2, p300/CBP, TAF1, TAF1L, Ash1L, MLL, SMARCA2, SMARCA4, BRPF1, ATAD2, BRD7, BRD2, BRD3, BRD4, BRDT, BAZ1B (WSTF), BAZ2B, BPTF, SP140L, TRIM24, and TRIM33.

The compounds provided herein are also useful for modulating gene transcription in a patient. Gene transcription can be modulated by inhibiting recruitment of bromodomain containing transcriptional co-activators, transcription regulator proteins, or chromatin remodeling regulator proteins; inhibiting lysine acetylation of histones, transcription regulator protein, or chromatin remodeling regulator proteins; and/or inhibiting interactions between of bromodomain containing transcriptional co-activators, transcription regulator proteins, or chromatin remodeling regulator proteins in complexes that are required for gene transcription.

In some embodiments, the transcriptional activity of NF-kB and its target genes are modulated. The compounds and compositions described herein can be useful in the treatment of diseases where NF-kB is over activated, such as cancer, inflammatory disease, auto-immune disease, cardiovascular disease, neurological disorders, and metabolic disorders.

In some embodiments, the transcriptional activity of IL6 and its target genes are modulated.

In some embodiments, the transcriptional activity of human p53 and activation of its target genes are modulated by the compounds and compositions provided herein. In some embodiments, the modulation is down regulation of the transcriptional activity. For example, such down regulation can enhance the reprogramming efficiency of induced pluripotent stem cells using one or more stem cell factors selected from Oct3/4, Sox2, Klf4, and c-Myc. Accordingly, the compounds and compositions can be useful in the treatment of disease or condition wherein p53 activity is hyper-activated under a stress-induced event such as trauma, hyperthermia, hypoxia, ischemia, stroke, a burn, a seizure, a tissue or organ prior to transplantation, or a chemo- or radiation therapy treatment.

In some embodiments, the transcriptional activity of PCAF is modulated by the compounds and compositions provided herein. For example, such modulation can be useful in the treatment of HIV/AIDS in a patient.

In some embodiments, the compounds and compositions provided herein can be useful in the regulation of P-TEFb in a patient. For example, P-TEFb can be regulated by binding one or more bromodomains of BRD4.

In some embodiments, the transcriptional activity of transcription co-activators CBP/p300 by binding to the bromodomain is modulated by the compounds and compositions provided herein. For example, the compounds and compositions can be useful in the treatment of disease or condition wherein CBP/p300 activity is inducing or promoting the disease or condition including cancer, acute myeloid leukemia (AML), chronic myeloid leukemia, circadian rhythm disorders, or drug addiction.

In some embodiments, the transcriptional activity of Williams-Beuren syndrome transcription factor (WSTF) by binding to the bromodomain is modulated by the compounds and compositions provided herein. In some cases, the compounds and compositions are useful in the treatment of disease or condition wherein WSTF hyper-activity in overexpressed vitamin A receptor complexes is implicated, for example, in cancer of the breast, head and neck, and lungs, as well as leukemia and skin cancers.

In some embodiments, the compounds and compositions provided herein are useful for promoting lineage progression of adult stem cells. For example, the compounds can inhibit the lysine acetylation of histones, transcription regulator proteins, transcriptional co-activators, or other chromatin-associated proteins by bromodomain containing histone acetyltransferase (HAT) transcriptional co-activators. Inhibition lysine acetylation can promote the lineage progression of oligodendrocyte progenitor cells toward a differentiated state. This promotion can be useful for promoting neural repair in a patient and in the treatment of a neurodegenerative autoimmune disease in a patient.

The compounds and compositions herein are also useful for inducing myelination of a neuron. For example, in a patient diagnosed with a neurodegenerative autoimmune disorder or a demyelinating disorder.

Non-limiting examples of diseases and disorders that can be treated using the compounds and compositions provided herein include, for example, HIV/AIDS, cancer, inflammatory disease, auto-immune disease, cardiovascular disease (e.g., myocardial hypertrophy), neurological disorders (e.g., Alzheimer's disease and Parkinson's disease), metabolic disorders (e.g., type 2 diabetes mellitus), a disease or condition wherein p53 is hyper-activated under a stress-induced event, circadian rhythm disorders, drug addiction, and neurodegenerative auto-immune disease.

Cancers that may be treated by the compound, compositions and methods described herein include, but are not limited to, the following: B cell lymphoma, Hodgkin's disease, T cell lymphoma, adult T cell lymphoma, adult T cell leukemia, acute lymphoblastic leukemia, breast cancer, liver cancer, thyroid cancer, pancreatic cancer, prostate cancer, melanoma, head and neck SCC, colon cancer, multiple myeloma, ovarian cancer, bladder cancer, lung carcinoma. In some embodiments, the compounds and compositions provided herein are administered before, after, or in combination with a therapeutically effective amount of an anticancer agent. The anticancer agent can include, for example, irinotecan, daunorubicin, doxorubicin, vinblastine, vincristine, etoposide, actinmycin D, cisplatin, paclitaxel, gemcitabine, SAHA, and combinations thereof. In some embodiments, the patient suffering from cancer is resistant to one or more cytotoxic chemotherapeutic agent.

Stem cell differentiation can also be induced by the compounds and compositions provided herein. For example, the stem cells can include cancer stem cells. In some embodiments, the compounds provided herein can induce apoptosis of malignant cells in a patient.

Inflammatory diseases that can be treated by the compound, compositions and methods described herein include, but are not limited to, the following: rheumatoid arthritis, inflammatory bowel disease, multiple sclerosis, type 1 diabetes, lupus, asthma, psoriasis, sepsis, gastritis, and post ischemic inflammation (e.g., stroke and myocardial infarction).

Neurodengenerative autoimmune diseases that can be treated by the compounds and compositions provided herein include, but are not limited to, the following: multiple sclerosis, acute disseminated encephalomyelitis, transverse myelitis, chronic inflammatory demyelinating polyneuropathy, Guillain-Barré syndrome, central pontine myelinosis, and inherited demyelinating diseases. In addition, the compounds and compositions provided herein can be useful for treating a demyelinating disorder. Such a disorder includes any disease of the nervous system in which the myelin sheath of neurons is damaged. This damage impairs the conduction of signals in the affected nerves, causing impairment in sensation, movement, cognition, or other functions depending on which nerves are involved. Examples of demylelinating disorders include multiple sclerosis, vitamin $B_{12}$ deficiency, Tabes Dorsalis, transverse myelitis, Devic's disease, progressive multifocal leukoencephalopathy, Optic neuritis, Leukodystrophies, Guillain-Barré syndrome, anti-MAG peripheral neuropathy, Charcot-Marie-Tooth Disease, and copper deficiency.

The compounds and compositions described herein can be administered before, after, or in combination with a therapeutically effective amount of a histone acetyltransferase (HAT) inhibitor. Non-limiting examples of HAT inhibitors include anacardic acid, garcinol, curcumin, and quinolones. See, for example, F. Manzo et al., *Expert Opin Ther Pat.* (6):761-74 (2009).

In some embodiments, the methods described herein can be used in vitro, for example, increasing myelination of a neuron, modulating gene transcription in a cell, modulating the transcriptional activity of PCAF in HIV transcriptional activity and replication in a cell, inhibiting transcriptional activity of NF-kB, inducing stem cell differentiation in a cell, inducing apoptosis in a malignant cell, regulating P-TEFb, modulating transcriptional activity of human p53 and activation of its target genes in a cell, modulating the transcriptional activity of transcription co-activators CBP/p300 in a cell, and modulating the transcriptional activity of WSTF in a cell. Such in vitro methods can be performed by contacting a cell or neuron with an effective amount of a compound of formula (1) and/or formula (2). Uses of such in vitro methods include, but are not limited to, use in a screening assay (for example, wherein the compound is used as a positive control or standard compared to compounds of unknown activity or potency in any of the methods provided herein).

EXAMPLES

Chemicals and General Procedure.

Commercially available reagents and solvents were obtained from Aldrich Chemical Co. (Milwaukee, Wis.), Fluka Chemical Corp. (Milwaukee, Wis.), TCI America (Portland, Oreg.), Ark Pharm (Livertyville, Ill.) and Acros Organics USA (Morris Plains, N.J.). They were used without any further purification. Reactions were monitored by analytical thin-layer chromatography (TLC) and LC/MS. TLC analysis was performed using Merck silica gel 60 F254 plates. LC/MS analysis was carried out on an Agilent 1100 Series HPLC equipped with a ZORBAX Eclipse XDB-18 analytical column from Agilent (4.6×150 mm, 5 mm) and attached to a TOF mass detector equipped with an electrospray ionization source (ESI). A gradient method using $H_2O/0.1\%$ formic acid (Solvent A) and Acetonitirle/0.1% formic acid (Solvent B) as eluent solvent was implemented with a flow rate of 0.4 mL/min, column temperature at 30° C., UV detection at 210 nm, 254 nm and 280 nm. The gradient method was run in 7 minutes with Solvent A from 90% to 1% and Solvent B from 1% to 99%. Purification was carried out using a SP1 purification system (Biotage) with pre-packed FLASH silica columns.

Example 1—General Synthetic Procedure

The synthesis of the compounds was achieved in four synthetic steps using schemes as illustrated below in Scheme 3.

Scheme 3.

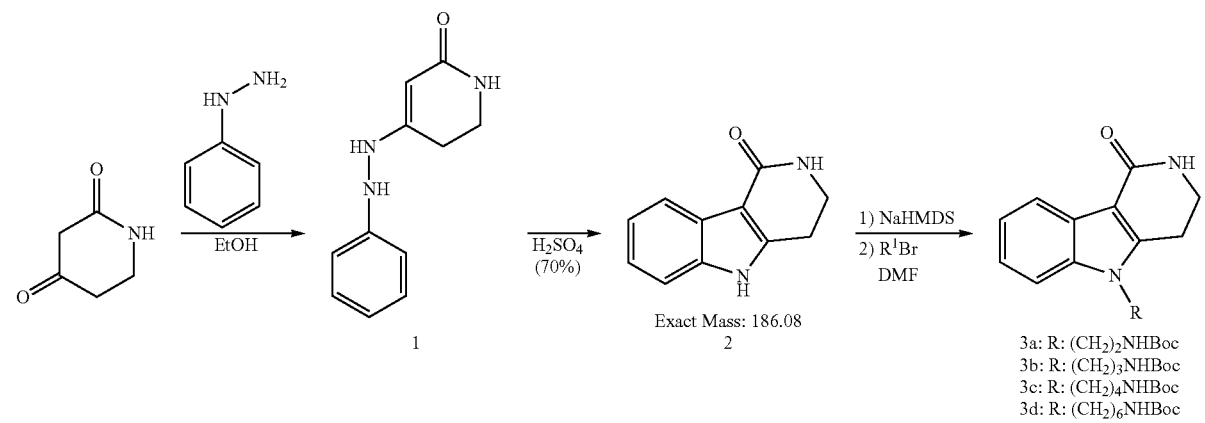

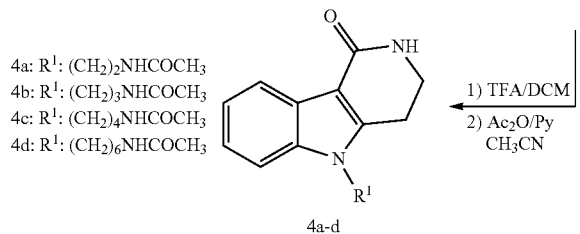

4a: R¹: (CH₂)₂NHCOCH₃
4b: R¹: (CH₂)₃NHCOCH₃
4c: R¹: (CH₂)₄NHCOCH₃
4d: R¹: (CH₂)₆NHCOCH₃

1) TFA/DCM
2) Ac₂O/Py
CH₃CN 4a-d

Briefly, compound 1 was prepared by reaction of phenylhydrazine with commercially available 2,4-piperidinedione in ethanol under nitrogen atmosphere. Next, the pyridoindole scaffold was constructed following the Fisher indole synthesis, by treatment of phenylhydrazone 1 with sulfuric acid (70%) (see Rodriguez, J.-G. & Temprano, F. J., *J. Chem. Soc. Perkins Trans. I*, 2117-2122 (1989)). The use of other acids such as formic acid, acetic acid, hydrochloric acid or trifluoroacetic acid, which are successfully applied in the Fisher indole synthesis of different substituted indoles, did not produce the expected pyrido-indole ring 2 under different reaction conditions (Barbieri, V. & Grazia, M. F., *Tetrahedron Letters* 47, 8289-8292 (2006); Gribble, G. W., *Contemp. Org. Synth.* 1, 145-172 (1994); and Li, X. & Vince, R., *Bioorg. & Med. Chem.* 14, 2942-2955 (2006)). The 2,3,4,5-tetrahydro-1H-pyrido-[4,3-b]indol-1-one 2 was then N-alkylated with the suitable tert-butoxycarbonyl-protected alkyl bromide, using lithium bis(trimethylsilyl) amide as a base (see Coldham, I. et al., *Eur. J. Org. Chem.*, 2676-2686 (2007)). Other bases such as KOH, NaH or BuLi also led to the correspondent N-alkylated products but with lower yields (Miyamoto, H. et al., *Tetrahedron Letters* 48, 1805-1808 (2007); Lee, K. L. et al., *J. Med. Chem.* 50, 1380-1400 (2007); and Fukuda, T. & Maeda, K., *Tetrahedron* 55, 9151-9162 (1999)). Finally, treatment of N-tert-butoxycarbonyl substituted pyrido-indoles with trifluoroacetic acid and subsequent acetylation with acetyl chloride/propylene oxide afforded the final compounds 4a-d with good yields. More detailed experimental conditions and procedures are described below.

Example 2—Preparation of 5,6-Dihydro-4-(2-phenylhydrazino)-2(1H)pyridine (1)

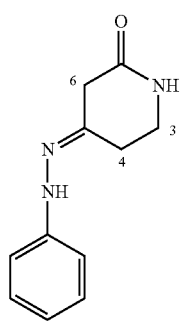 [SMILES: O=C1C/C(=N/Nc2ccccc2)CCN1]

Phenylhydrazine (0.880 mL, 8.84 mmol) was added over 5 minutes to a stirred solution of 2,4-piperidinedione (1 g, 8.84 mmol) in 10 mL of ethanol under nitrogen atmosphere. After 1 h of stirring at room temperature, the resulting suspension was filtered and the solid was then washed with cold water and diethyl ether, to afford 1.60 g (82%) of the title compound.

Example 3—Preparation of 2,3,4,5-tetrahydro-1H-pyrido-[4,3-b]indol-1-one (2)

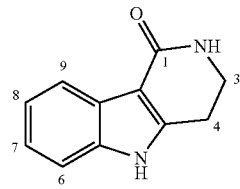 [SMILES: O=C1NCCc2[nH]c3ccccc3c21]

A solution of 5,6-Dihydro-4-(2-phenylhydrazino)-2(1H) pyridine (1 g, 4.93 mmol) was added portion-wise to a ice-cold mixture of sulfuric acid (3.5 mL) and water (1.5 mL). The reaction progress was monitored by TLC (~3 h), then neutralized with ice-cold sodium hydroxide (20 mL, 2M) and extracted with EtOAc. The organic phases were combined, washed with brine, dried over sodium sulfate, filtered and evaporated to dryness. Purification by column chromatography, eluting with CH₂Cl₂/MeOH (15:1) gave 0.65 g (65%) of the indole 2 as a solid.

Example 4—General Procedure for the Preparation of N-alkylated-pyridoindoles (3)

NaHMDS (0.8 mL, 0.8 mmol of a 1.0 M solution in THF) was added to a solution of 2,3,4,5-tetrahydro-1H-pyrido-[4,3-b]indol-1-one (0.1 g, 0.533 mmol) in DMF (5 mL) at −78° C. under nitrogen. After 30 min stirring at −78° C., a solution of the correspondent alkylating agent (0.8 mmol) in DMF (1 mL) was added dropwise and the mixture was warmed at room temperature and then heated at 90° C. for 12 h. Saturated aqueous NaHCO₃ was then added to the reaction mixture and the resulting suspension was extracted with EtOAc three times. The combined organic layers were washed with brine and dried with Na₂SO₄. Filtration and concentration in vacuum afforded the corresponding N-alkyl-pyridoindole (3), which was purified by column chromatography.

2,3,4,5-tetrahydro-1-(2-tert-butoxycarbonylamino-ethyl)-pyrido-[4,3-b]indol-1-one (3a)

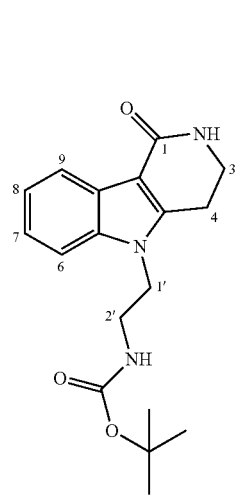

Alkylating reagent: 2-(t-butoxycarbonylamino)ethyl bromide (0.18 g, 0.8 mmol). Column chromatography: Eluted with $CH_2Cl_2$/MeOH (15:1) to give 0.083 g (47%) of the indole 3a as an oil.

2,3,4,5-tetrahydro-1-(3-tert-butoxycarbonylamino-propyl)-pyrido-[4,3-b]indol-1-one (3b)

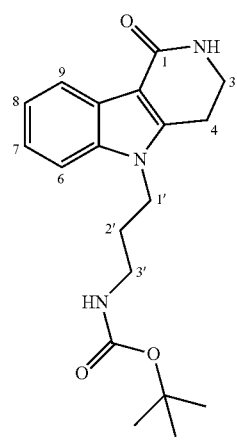

Alkylating reagent: 3-(t-butoxycarbonylamino)propyl bromide (0.19 g, 0.8 mmol). Column chromatography: Eluted with $CH_2Cl_2$/MeOH (15:1) to give 0.109 g (61%) of the indole 3b as an oil.

2,3,4,5-tetrahydro-1-(4-tert-butoxycarbonylaminobu-tyl)-pyrido-[4,3-b]indol-1-one (3c)

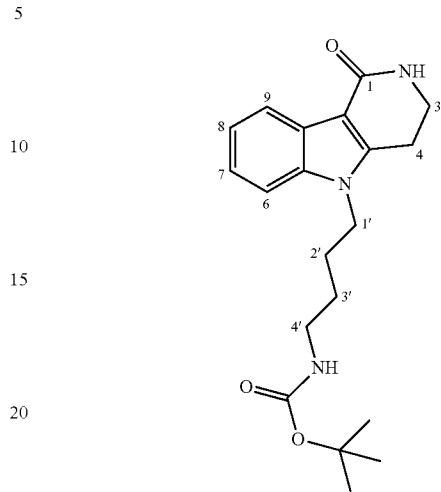

Alkylating reagent: 4-(t-butoxycarbonylamino)butyl bromide (0.20 g, 0.8 mmol). Column chromatography: Eluted with $CH_2Cl_2$/MeOH (15:1) to give 0.105 g (55%) of the indole 3c as a solid.

2,3,4,5-tetrahydro-1-(4-tert-butoxycarbonylaminobu-tyl)-pyrido-[4,3-b]indol-1-one (3d)

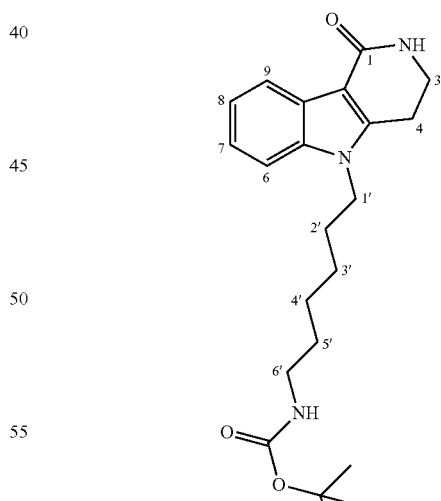

Alkylating reagent: 6-(t-butoxycarbonylamino)hexyl bromide (0.22 g, 0.8 mmol). Column chromatography: Eluted with $CH_2Cl_2$/MeOH (15:1) to give 0.0878 g (44%) of the indole 3d as a solid.

2,3,4,5-tetrahydro-5-[(N-tert-butoxycarbonyl)amino-propylthiocarbamoyl]-1H-pyrido-[4,3b]-indol-1-one (3e)

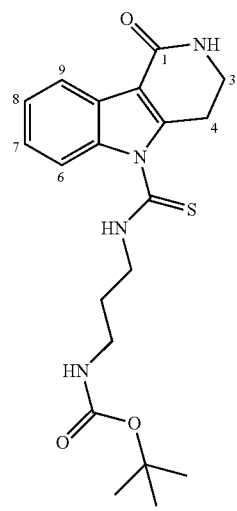

Alkylating reagent: N-Boc-3-isothiocyanatopropylamine (0.17 g, 0.8 mmol). Column chromatography: Eluted with CH$_2$Cl$_2$/MeOH (15:1) to give 0.17 g (61%) of the indole 3e as an oil.

2,3,4,5-tetrahydro-5-[N-(4-acetylphenyl)carbamoyl-methyl)]-1H-pyrido-[4,3-b]indol-1-one (3f)

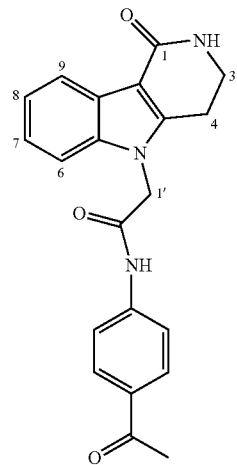

Alkylating reagent: N-(4-Acetylphenyl)-2-chloroacet-amide (0.17 g, 0.8 mmol). Column chromatography: Eluted with CH$_2$Cl$_2$/MeOH (15:1) to give 0.17 g (61%) of the indole 3f as a solid.

Example 5—General Procedure for N-Boc Deprotection and Acetylation of N-alkylated-pyridoindoles (4)

Trifluoroacetic acid (1 mL) was added to a solution of the correspondent 5-substituted-2,3,4,5-tetrahydro-1H-pyrido-[4,3-b]indol-1-one (3) in CH$_3$CN (10 mL). The solution was stirred at room temperature for 30 min and then the solvent was evaporated. The resulting oil was co-evaporated with CH$_2$Cl$_2$ until the remaining TFA was removed. Next, the resulting oil was dissolved in CH$_3$CN. Propylene oxide (10 eq) and acetyl chloride (1.5 eq) was then successively added and after 1 h of stirring at room temperature the solvent was evaporated to dryness. The resulting oil was purified by column chromatography.

2,3,4,5-tetrahydro-5-(2'-acetamidoethyl)-1H-pyrido-[4,3-b]indol-1-one (4a)

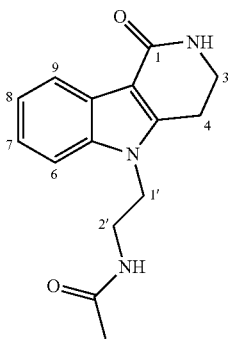

From 3a (0.05 g, 0.152 mmol). Column chromatography: Eluted with CH$_2$Cl$_2$/MeOH (15:1) to give 0.035 g (85%) of the acetyl-substituted indole 4a as an oil.

2,3,4,5-tetrahydro-5-(3'-acetamidopropyl)-1H-pyrido-[4,3-b]indol-1-one (4b)

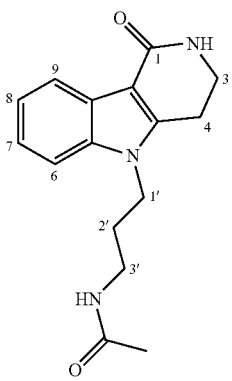

From 3b (0.05 g, 0.145 mmol). Column chromatography: Eluted with CH$_2$Cl$_2$/MeOH (15:1) to give 0.032 g (78%) of the acetyl-substituted indole 4b as an oil.

2,3,4,5-tetrahydro-5-(4'-acetamidobutyl)-1H-pyrido-[4,3-b]indol-1-one (4c)

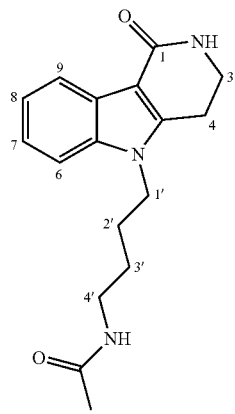

From 3c (0.05 g, 0.14 mmol). Column chromatography: Eluted with $CH_2Cl_2$/MeOH (15:1) to give 0.037 g (90%) of the acetyl-substituted indole 4c as a solid.

2,3,4,5-tetrahydro-5-(6'-acetamidohexyl)-1H-pyrido-[4,3-b]indol-1-one (4d)

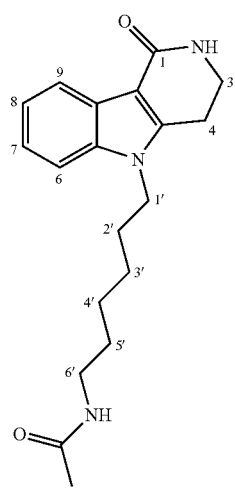

From 3d (0.05 g, 0.13 mmol). Column chromatography: Eluted with $CH_2Cl_2$/MeOH (15:1) to give 0.031 g (74%) of the acetyl-substituted indole 4d as solid.

2,3,4,5-tetrahydro-5-[(N-acetyl)aminopropylthiocarbamoyl]-1H-pyrido-[4,3-b]indol-1-one (4e)

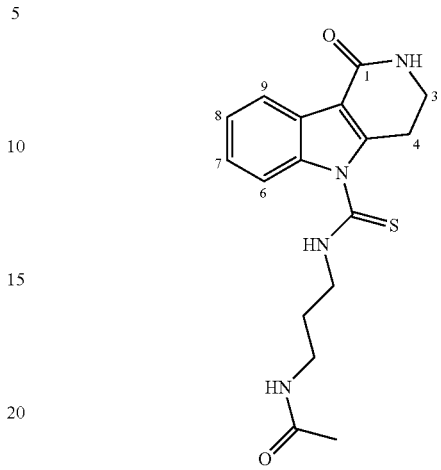

From 3d (0.05 g, 0.124 mmol). Column chromatography: Eluted with $CH_2Cl_2$/MeOH (15:1) to give 0.031 g (73%) of the indole 4e as oil.

Example 6—In Vitro Fluorescence Polarization-Based Binding Assay

Expression and purification of the recombinant CBP BRD in poly-his tag form was conducted using the procedure as previously described (Mujtaba, S. et al., *Mol Cell* 13, 251-63 (2004)). The purified protein was confirmed with mass spectroscopy. Binding assays were performed with CBP BRD (5 μM) and fluorescent probe (10 nM), and increasing concentration of unlabeled competing ligand.

As shown in FIG. 1, compound 4a, containing the shorter N-alkylated chain, showed the lowest improvement of the series. Increasing the length of the N-alkylated chain from two to four methylene groups resulted in a 7-fold enhancement of the binding (4c vs. 4a), whereas a further extension led to partial or total loss of the affinity (4d). The best compound of the series 4c, which we have named 4c, exhibited an $IC_{50}$ better than 5 μM, which is the sensitivity limit of the assay. This represents a greater than 12-fold improvement in binding affinity as compared to the initial lead MS7972.

Example 7—Protein Crystallization and X-Ray Diffraction Data Collection

Purified CBP BRD protein (15 mg/mL) was mixed with compound 4c at 1:10 molar ratio of protein:compound. The complex was crystallized using the sitting drop vapor diffusion method by mixing 1 μL of protein solution with 1 μL of the reservoir solution that contains 15% PEG 3,350, 0.1 M magnesium acetate, 0.1 M HEPES pH 7.5, and 5% glycerol. Crystals were soaked in the corresponding mother liquor supplemented with 20% glycerol as cryoprotectant before freezing in liquid nitrogen. X-ray diffraction data were collected at 100K at beamline X6A of the National Synchrotron Light Source (NSLS) at Brookhaven National Laboratory. Data were processed using the HKL-2000 suite. The structure of the CBP BRD was solved by molecular replacement using the program MOLREP, and the structure refinement was done using the program Refmac. Graphics program COOT was used for model building and visualization. Crystal diffraction data and refinement statistics for the structure are displayed in Table 1.

| Data collection | |
|---|---|
| Space group | P 1 21 1 |
| Cell dimension | |
| a, b, c (Å) | 48.0, 33.0, 70.3 |
| α, β, γ(°) | 90, 107.2, 90 |
| Resolution (Å) | 20-1.70 |
| $R_{merge}$ (%) | 5.8 (37.1)[b] |
| I/σ | 26 (4.8) |
| Completeness (%) | 99.8 (98.6) |
| Redundancy | 3.4 (3.6) |
| Refinement | |
| Protomers per asymmetric unit | 2 |
| Resolution (Å) | 20-1.70 |
| No. reflections | 22,171 |
| $R_{work}/R_{free}$ (%) | 18.6/23.2 |
| No. atoms | |
| Protein | 903 |
| Ligand/peptide/ion | 10 |
| Water | 81 |
| B-factors | |
| Protein | 28.0 |
| Ligand/peptide/ion | 61.3 |
| Water | 36.4 |
| R.m.s. deviations | |
| Bond length (Å) | 0.005 |
| Bond angles (°) | 1.0 |

[a]See Methods section for exact experimental conditions.
[b]Values in parentheses are for highest-resolution shell.

Example 8—Molecular Dynamics (MD) Simulations of CBP BRD/Ligand Complexes

MS7972 was identified in a NMR-based screening and was used as a lead compound. 20 ns molecular dynamics (MD) simulations of the NMR structure of the CBP BRD/MS7972 complex (PDB ID 2D82) was performed, and it was observed that the ligand keeps a stable bound pose ~80% of the MD simulation (FIG. 2A), which satisfies the NOE-derived distance constraints. This MD simulation model was used to guide the structure-based ligand design to improve affinity of MS7972 to the CBP BRD.

20 ns MD simulations were also performed with the crystal structure of the CBP BRD bound to compound 4c. During the MD simulation, all tritatable groups in the protein were treated charged (excluding histidine that is not present in the CBP BRD). The all-atom Amber force field and the TIP3P water model were used in all calculations. The system was initially minimized using the Steepest Descent and Conjugates Gradients methods to remove all the possible unfavorable interactions from the crystal structure. Then, it was heated to 300 K for 100 ps by increasing the temperature 20 K every 1 ps during the first 10 ps. After heating, a sequence of minimization and equilibration with positional restraints on the protein and the ligand, which were reducing gradually from 25 kcal/mol until allow the system to move freely, were performed. Twin-range non-bonded cutoff of 10 Å and 12 Å were used for the Lennard-Jones potentials and electrostatic interactions were calculated using particle-mesh Ewald. The production MD simulation was carried out for 20 ns using NPT ensemble. In the production stage the temperature was maintained using the Berendsen (weak-coupling) method with a temperature coupling parameter of 5 ps. The length of all bonds involving hydrogen atoms was kept fixed with the SHAKE algorithm. The pressure was kept fixed to 1 atm. The equations of motion were integrated with a time-step of 2 fs. A periodic boundary truncated octahedron unit cell was used throughout (63.1×63.1×63.1 Å/a=109.5, b=109.5 and g=109.5). The coordinates were saved every 1 ps. All MD simulations and analysis were performed using the Amber and Simulaid programs. The CBP BRD/4c simulation was stable and the ensemble of structures is within 2.8 Å RMSD, which includes all atoms for the whole 20 ns MD trajectory providing the basis for an analysis of a stable complex (see FIG. 2B). Two key hydrogen bond interactions are revealed during the MD simulation, which are between the side chains of Asn1168 and Arg1173 in CBP and the carbonyl oxygen of the acetyl group and the ring carbonyl group of 4c, respectively. The latter was indeed observed in the crystal structure of the complex. The main residue contributions to the interaction energy between CBP BRD and 4c are listed in Table 2.

TABLE 2

| | CBP BRD/4c (kcal/mol) |
|---|---|
| Leu1109 | −1.87 ± 0.32 |
| Pro1110 | −4.37 ± 0.41 |
| Phe1111 | −1.29 ± 0.36 |
| Val1115 | −1.35 ± 0.52 |
| Leu1120 | −1.81 ± 0.37 |
| Ile1122 | −1.02 ± 0.24 |
| Tyr1125 | −1.72 ± 0.44 |
| Ala1164 | −1.17 ± 0.31 |
| Tyr1167 | −1.89 ± 0.35 |
| Asn1168 | −4.18 ± 0.33 |
| Arg1173 | −5.90 ± 1.45 |
| Val1174 | −3.97 ± 0.51 |
| Phe1177 | −0.41 ± 0.27 |

Figure 2:
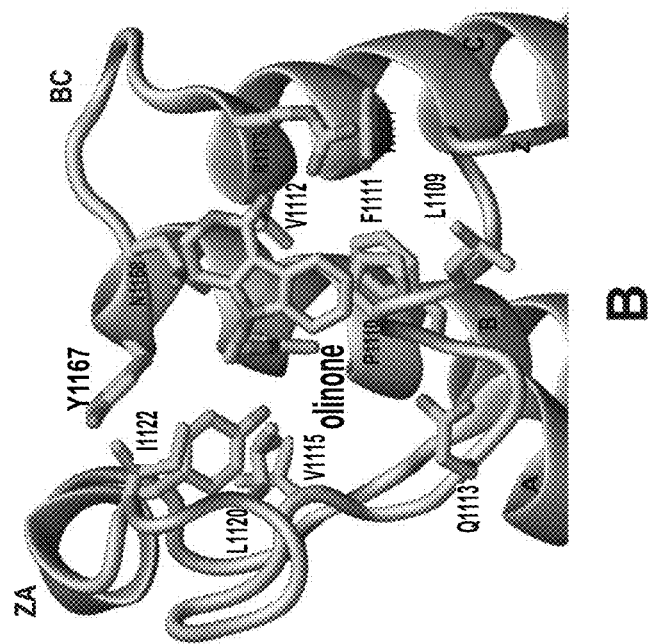
FIG. 2 is a representation of the conformation of the CBP BRD/MS7972 complex (FIG. 2A) and the conformation of the CBP BRD inhibitor (4c; olinone), calculated by MD simulations (FIG. 2B).
Figure 2:
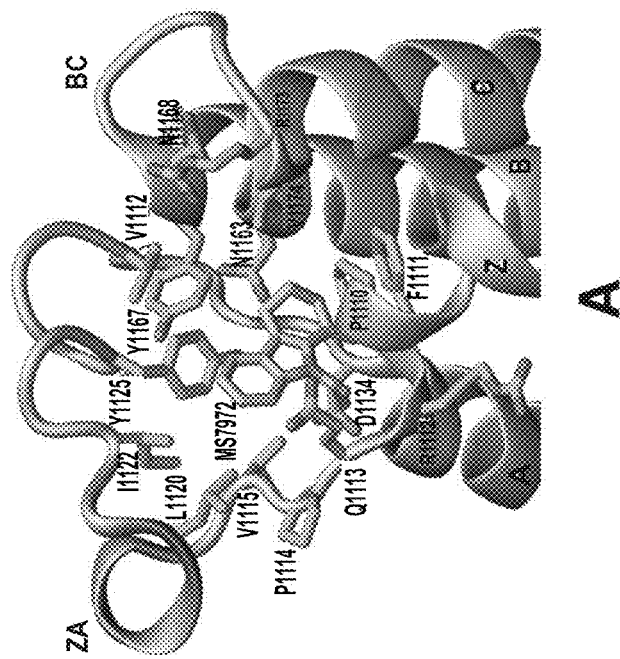
Figure 3:
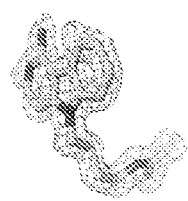
FIG. 3A shows the binding of 4c by CBP BRD.
FIG. 3B illustrates the orientation of 4c when bound to the BRD.
Figure 3:
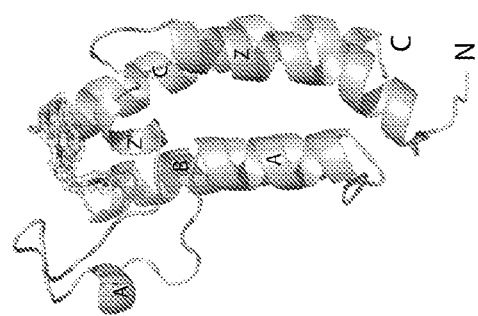
Figure 11:
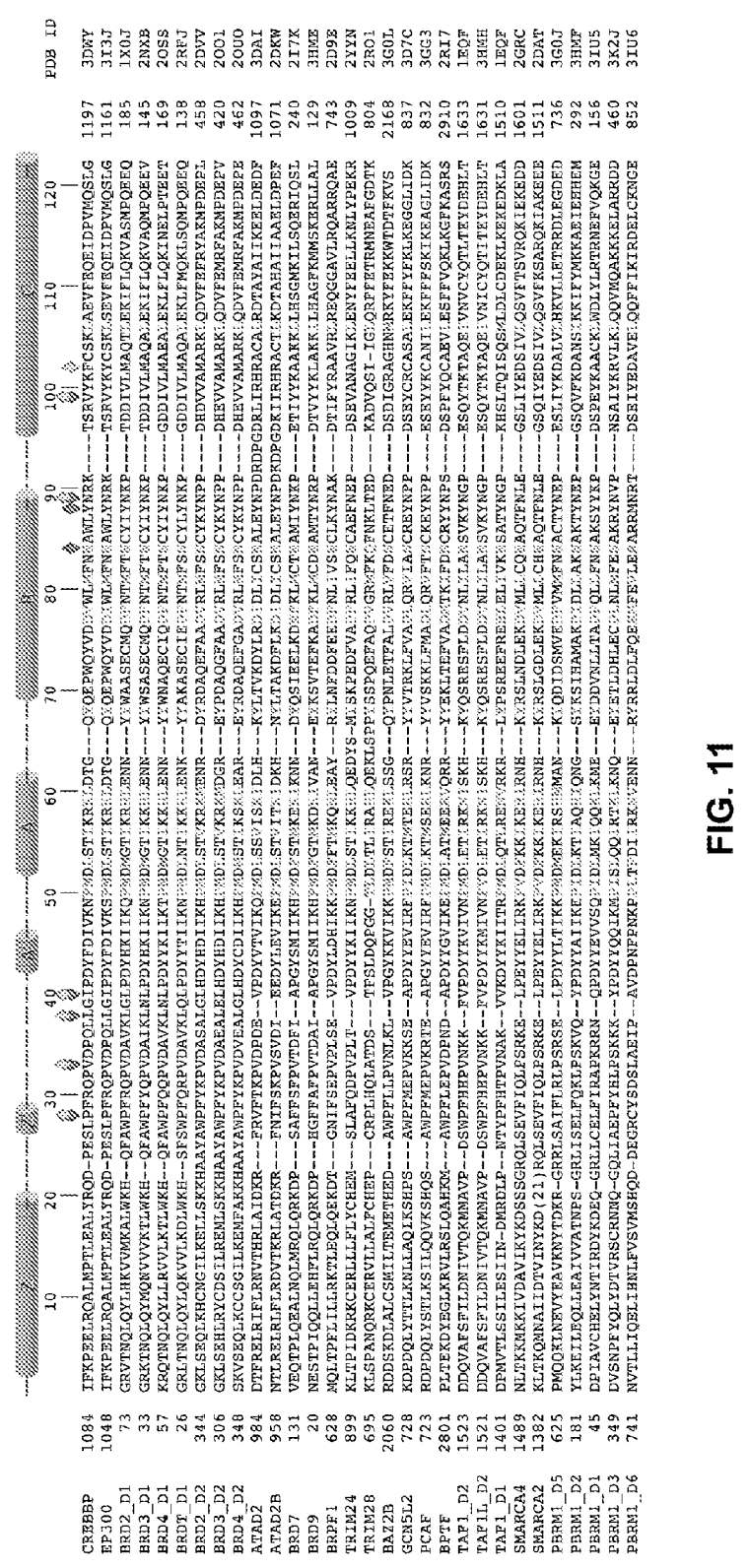
Figure 17:
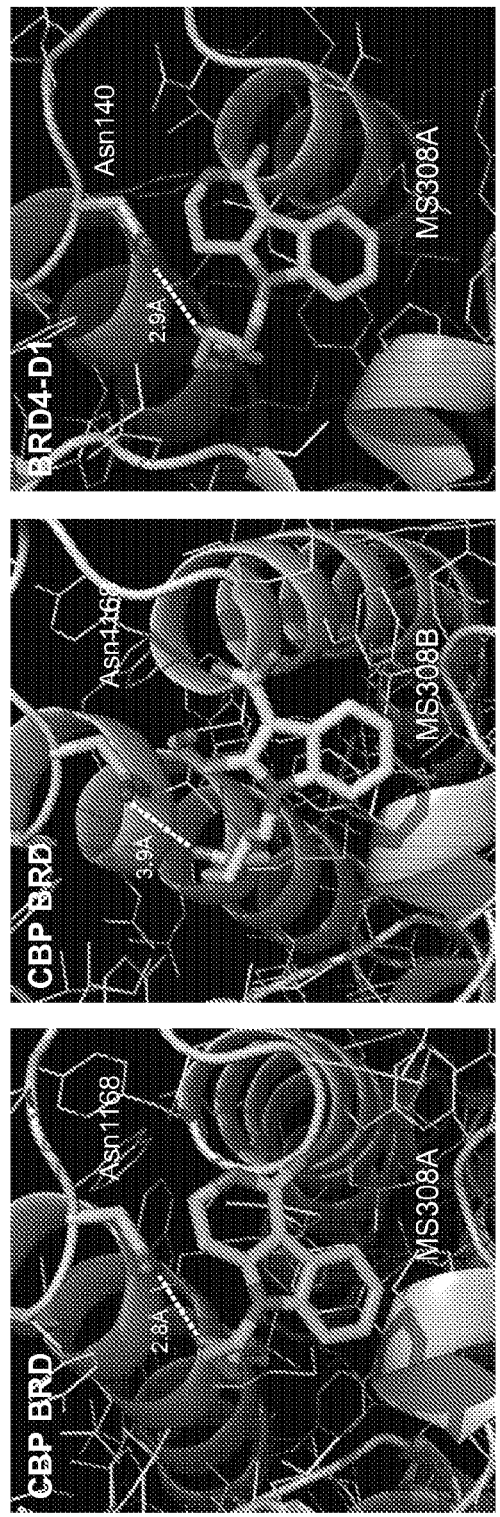
FIG. 17 shows the binding of 4c by CBP BRD and BRD4-D1.

The molecular basis of 4c recognition by CBP BRD was shown by the 1.7 Å resolution crystal structure of the protein/ligand complex (FIG. 3A). 4c forms a chair-like conformation in the bound state (FIG. 3B); its tri-heterocyclic moiety as the seat packs against the side chain of Pro 1110 of the one-turn helix Z' and interacts with Val1174 and Phe1177 at the opening of the acetyl-lysine binding pocket formed between the ZA and BC loops. The acetyl chain of 4c, as its back, intercalates into a hydrophobic pocket lined with Val1115, Leu1120, Ile1122 and Tyr1125 of the ZA loop. The carbonyl oxygen of the acetyl group of 4c forms a hydrogen bond (2.8 Å) to the amide nitrogen of the highly conserved Asn1168 in CBP. Another stable electrostatic interaction was observed in the MD simulations of the complex between Arg1173 and the carbonyl group of the piperidone ring of ligand (FIG. 2B). Given that some ligand binding residues in CBP such as Arg1173 and Phe1177 are not conserved in the human BRD family (FIG. 11), the new structure suggests that 4c may be selective for the CBP BRD over the BRDs of other transcriptional proteins (FIG. 17).

Example 9—Promotion of Linear Progression of Oliogodendrocytes Primary Oligodendrocyte Cultures Cortex from rat p1 pups were dissected in L-15 medium and collected in NM10 medium (DMEM+10% FBS+2 mM glutamine+1 mM sodium pyruvate+100 U/ml penicillin+100 μg/ml streptomycin). The dissociated cells were plated into 75 cm² flasks (1.5 brain per flask) and cultured at 37° C. supplied with 5% $CO_2$ for 7 days with the changing of fresh NM10 medium every other day. At day 8 the flasks were shaken for 16-18 h at 200 rpm and 37° C. and the medium containing the 'shaken-off' cells were collected. Oligodendrocyte progenitors (OPCs) were then isolated from the cell suspension by immunoselection using A2B5 antibodies followed by incubation with anti-immunoglobulin magnetic microbeads (50 nm in size and biodegradable) and separation using a high-gradient magnetic field generated by the permanent magnet in the MACS Separator unit (Miltenyi Biotec). The purified OPCs were plated in NM10 medium onto Lab Tek®II 8-well chamber slides (Nalge Nunc Inc.) at a density of $2 \times 10^4$ per well for immunocytochemistry, or poly-D-lysine-coated 6-well plates at a density of $2 \times 10^5$ per well for RNA isolation. After incubated for 8-16 hr, the medium was changed to ODM (DMEM, 2 mM L-glutamine, 1 mM sodium pyruvate, 10 ng/ml biotin, 100 μg/ml apotransferrin, 100 μM putrescine, 20 nM progesterone, 30 nM sodium selenite, 5 μg/ml insulin, 100 U/ml penicillin, 100 μg/ml streptomycin) supplemented with bFGF (20 ng/ml) and platelet derived growth factor (PDGF; 10 ng/ml), and cultured for additional one day as previously described (He, Y. et al., *Neuron* 55, 217-30 (2007)). Oligodendrocyte differentiation was induced by culturing the cells in the same medium devoid of mitogens (ODM) with or without compounds at indicated concentrations. The medium was changed every 48 h and the cultures were preceded to immunocytochemistry after 2-day or 4-day differentiation, or RNA isolation after 4-day differentiation.

Immunocytochemistry.

Immunocytochemistry of cultured cells with O4 antibodies was performed live. Cells were gently rinsed in PBS (10 mM sodium phosphate, pH 7.4, and 150 mM NaCl) and incubated live with O4 hybridoma supernatant (1:10) for 30 min at 37° C. Cells were then fixed with 2% PFA for 20 min at room temperature and stained with secondary antibody goat anti-mouse IgM-Alexa Fluor 488 (Invitrogen) in blocking buffer (PGBA (0.1 M phosphate buffer, 0.1% gelatin, 1% bovine serum albumin. 0.002% sodium azide)+10% normal goat serum and Immunocytochemistry with anti-NG2 antibody (rabbit polyclonal, Chemicon #AB5320, 1:200 in blocking buffer) or anti-MBP (chicken, Ayes Labs #mbp, 1:400 in blocking buffer+0.5% Triton X-100) was performed on fixed cells and consisted of 1 hr incubation at room temperature or overnight at 4° C. After rinsing in PBS, sections were incubated with the appropriate secondary antibodies conjugated to Alex Fluro 546 for NG2 and Cy3 for MBP (Invitrogen and Jackson ImmunoResearch). DAPI (1:1,000; Molecular Probes, Inc.) was used as nuclear counterstain.

Image Acquisition and Quantification.

Images were captured at 20× objective using LSM 710 Meta confocal laser scanning microscope (Carl Zeiss Micro-Imaging, Inc.). For the quantification of the cells at different stages, three fields of each well and three wells of each condition were analyzed. To characterize the 2d culture, the number of each population NG2+, NG2; O4 double positive and O4+ was counted and summarized as total number of oligodendrocyte. The proportion of each population was calculated by referring to the total number of oligodendrocyte. To characterize the 4d culture, the percentage of MBP+ cells was calculated by dividing the number of MBP+ cells by the number of O4+ cells.

Quantitative RT-PCR.

Total RNA were isolated from the cells using Trizol® Reagent following manufacturer's instruction and cleaned up using RNeasy Mini kit (Qiagen, Hilden, Germany). 0.5-1 μg of total RNA was used in 20 μl of reverse transcription (RT) reaction, using SuperScript RT-PCR kit (Invitrogen, Carlsbad, Calif.). Quantitative RT-PCR was performed using Applied Biosystems SYBR green PCR master mix in 384-well plate in ABI 7900HT Sequence Detection PCR System. The PCR was performed in a 20 μl reaction mixture containing 0.2 μl cDNA as template and 100 nM specific oligonucleotide primer pairs using program denaturation at 95° C. for 15 s; annealing and extension at 60° C. for 1 min for 40 cycles. Melting curve of each sample was measured to ensure the specificity of the products. Data were normalized to the internal control GAPDH and analyzed using Pfaffl ΔΔCt method.

```
Primers used for mog are:
forward
                                         (SEQ ID NO: 31)
5'-GAGGGACAGAAGAACCCACA-3', reverse
                                         (SEQ ID NO: 32)
5'-CAGTTCTCGACCCTTGCTTC-3';

for GAPDH:
forward
                                         (SEQ ID NO: 33)
5'-AGACAGCCGCA-TCTTCTTGT-3', reverse
                                         (SEQ ID NO: 34)
5'-CTTGCCGTGG-GTAGAGTCAT-3'.

Lmnb1 primers Forward;
                                         (SEQ ID NO: 35)
AGCTCACCGGGCTCAAGGCT Reverse;
                                         (SEQ ID NO: 36)
AGCAGCAGCTGGTCGTGCTC.
```

Chromatin Immunoprecipitation.

Oligodendrocyte progenitors ($4 \times 10^6$) were crosslinked in 1% formaldehyde, lysed in nuclear lysis buffer (50 mM Tris-HCL (pH 8.0), 10 mM EDTA, 1% SDS, Protease Inhibitors (Roche) and PMSF) and sonicated using a Bioruptor (Diagenode) sonicator to produce chromatin with an average length of 500 base pairs. Chromatin was aliquoted and immunopreciptiated using protein A magnetic beads (Dynabeads-Invitrogen 100.01D) coated with 2 μg of antibodies to CBP (santa cruz sc-369), H3-K9ac (abcam ab4441), H3-K9ac and K14 (millipore 06-599), H3-K18ac (abcam ab1191). A mock immunopreciptitation was set-up as a control (No antibody). Immunoprecipitations were carried out overnight. Following immunoprecipitation, beads were washed 4 times with wash buffer (10 mM Tris-HCl (pH 7.5), 1 mM EDTA, 1 mM EGTA, 1% Triton X-100, 0.1% SDS, 0.1% Na-deoxycholate, 140 mM NaCl) and 2 times with TE buffer (10 mM Tris-HCl (pH 8.0), 10 mM EDTA) Immuno-precipitated chromatin and Input DNA were reverse crosslinked in elution buffer (20 mM Tris-HCl (pH 7.5), 5 mM EDTA, 50 mM NaCl, 1% SDS) with the addition of proteinase K (50 μg/ml) by heating (68° C.) and shaking (1,300 RPM) using a thermomixer (Eppendorf) for four hours. DNA was purified from the elution using phenol-chloroform followed by overnight ethanol precipitiation at −20° C. DNA was eluted in 200 μL of TE buffer.

Quantitative PCR was performed using primers to detect the transcriptional start site of the Lmnb1 promoter; forward 5'-CGGAGGGTCAGATTTTGAAT (SEQ ID NO:37), reverse 5'-GCCCGTAGC-ACTTTTGTTTC (SEQ ID NO:38). Sonciated chromatin from an unrelated sample was used to determine primer efficiency and as a reference for amount of DNA in each sample. The amount of Immunoprecipitated DNA was made relative to the amount of the input DNA for each sample.

Western Blot.

Oli-Neu cell line derived from mouse oligodendrocyte progenitors immortalized with the Neu antigen were grown on poly-ornithine-coated culture dishes and maintained proliferating in growth medium ODM plus 1% horse serum as previously described (He et al., 2007). Oli-Neu cells were induced to differentiation in ODM+0.5 mM dybutiryl-cAMP (Sigma) and treated together with CM000149 at indicated concentrations for one day. The cells treated with DMSO were used as the control. Total proteins from cultured cells were extracted using lysis buffer containing 50 mM Hepes (pH 7.4), 150 mM NaCl, 1% NP-40, 1 mM dithiothreitol (DTT), 1 mM EDTA, 0.01% phenylmethylsulfonyl fluoride (PMSF), 1 mM aprotinin and 1 mM leupeptin. Equal amount (40 µg) of proteins were loaded on 12% SDS-PAGE for separation and transferred onto PVDF (Millipore) membrane using a buffer containing 25 mM Tris base, pH 8.3, 192 mM glycine, 20% methanol for 1 hour at 100 V at 4° C. Western blot analysis was performed using the following antibodies at indicated dilution: anti-H3K9Ac (Abcam), 1:1,000; anti-H3K18Ac (Abcam), 1:1,000; anti-histone H3 (Abcam), 1:2,000; anti-acetyl-histone H3 (Upstate), 1:5,000; anti-α-tubulin, 1:10,000 (Sigma) and anti-acetylated-α-tubulin, 1:10,000 (Sigma). Immunoreactive bands were visualized using horseradish peroxidase-conjugated secondary antibodies (Amersham), followed by chemiluminescence with ECL-plus Western Blotting Detection System (Amersham).

Statistical Method—

Results are expressed as mean±standard deviation (SD) and statistically analyzed using two tailed Student's t tests. P of <0.05 was considered to be statistically significant. *p<0.05, p<0.01, *p<0.001.

Results—

Figure 4:
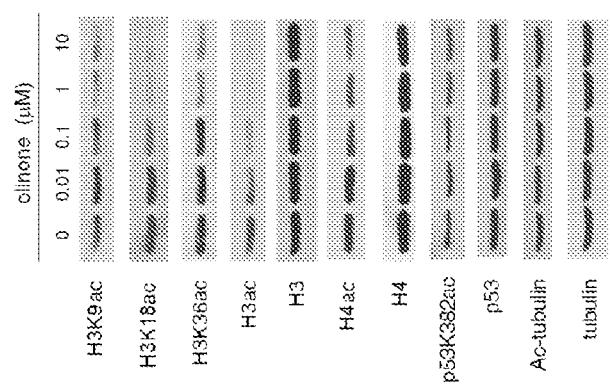
FIG. 4 illustrates the effects of dose-dependent 4c treatment (one day) of immortalized oligodendrocyte progenitors (Oli-Neu) on histone H3 acetylation and α-tubulin assessed by Western blotting using specific antibodies.
Figure 5:
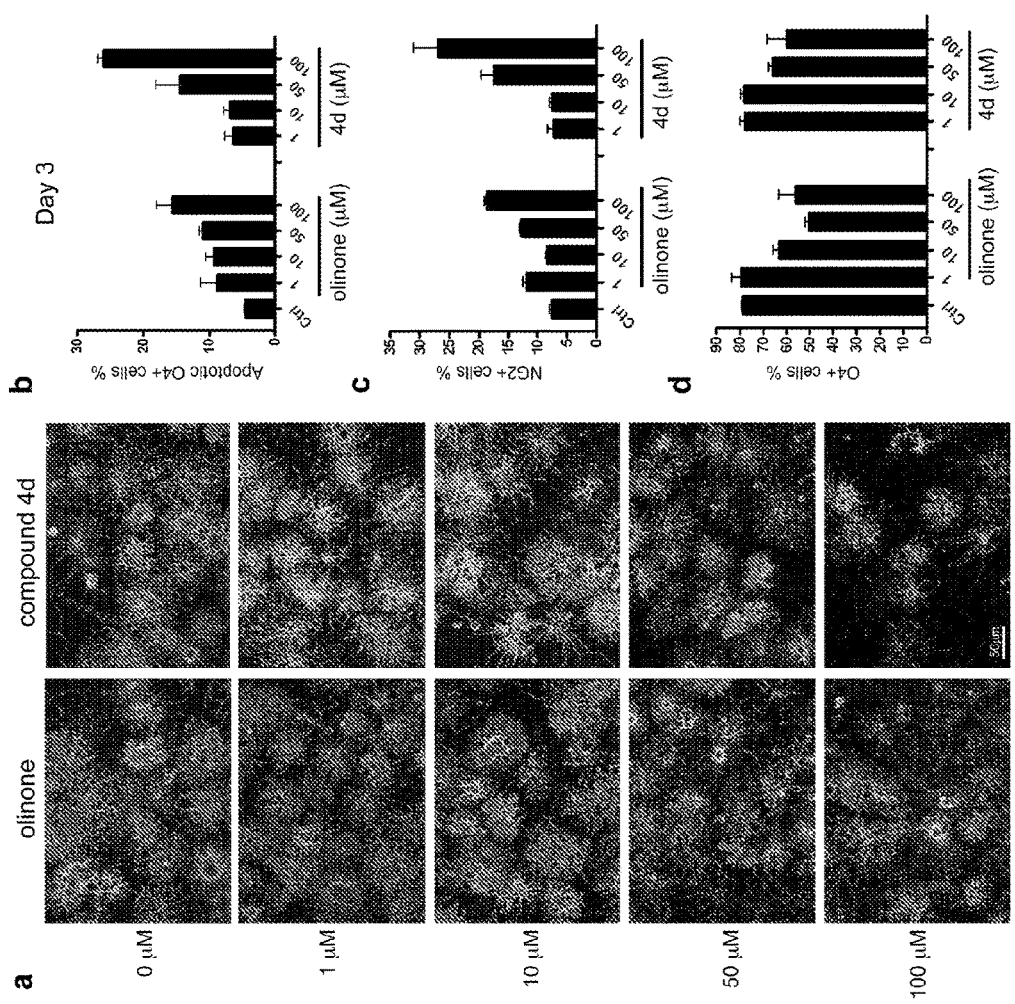
FIG. 5A shows the results of rat primary oligodendrocyte progenitors treated with 4c and 4d at indicated concentrations and induced to differentiate for 3 days. The cultures were immunostained for progenitor marker NG2 (dark) and intermediate marker O4 (light). The apoptotic cells were visualized by the degraded O4+ processes of the cells.
FIGS. 5b-d are bar graphs illustrating the proportion of each cell population quantified from duplicates with the mean±SD also presented.

The effect of 4c on CBP activity was tested in the oligodendrocyte-derived cell lines, which produced a decrease of global histone acetylation in a dose-dependent manner (FIG. 4). To assess the ability of 4c to modulate oligodendrocyte progenitor differentiation in primary cultures, its dose-dependent cytotoxicity was examined. Only at concentrations over 50 µM was significant cytotoxcity observed—more so with its analog 4d—as visualized by the degraded O4+ marker of the oligodendrocytes (FIG. 5).

Figure 6:
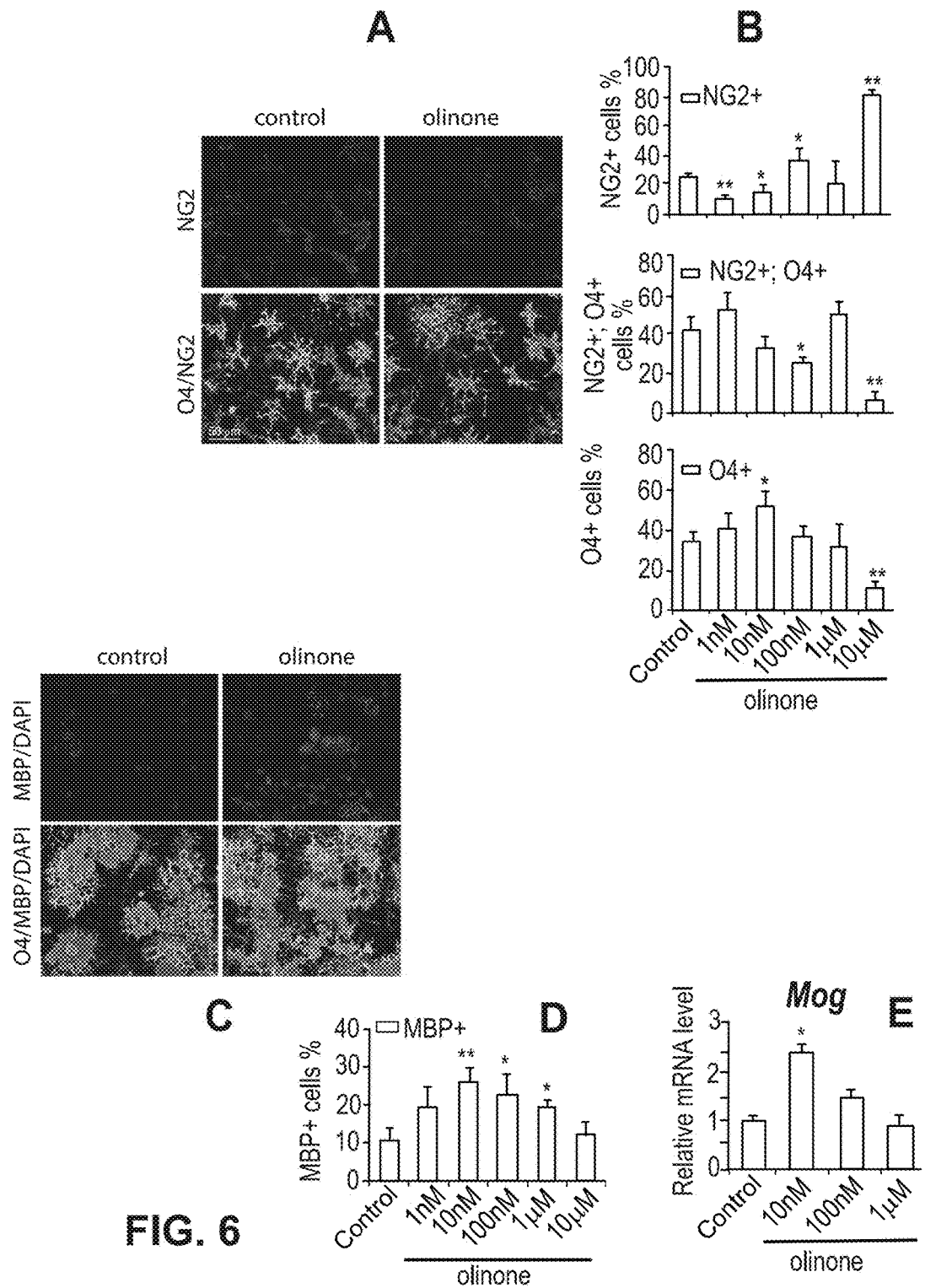
FIG. 6A shows the results of rat primary oligodendrocyte progenitors which were cultured in differentiation medium for 2 days in the absence (control) or presence of 4c (10 nM). Early and differentiating progenitors were identified by positive immunoreactivity for the marker NG2 (dark) or O4 (light), respectively.
FIG. 6B illustrates the number of NG2+, O4+ and NG2+/O4+ cells quantified in three independent experiments and the total number of oligodendrocyte lineage cells (mean±SD).
FIG. 6C illustrates the results of rat primary cells cultured in medium containing 4c (10 nM) for 4 days and then labeled with O4 (light) and with the differentiation marker MBP (dark).
FIG. 6D is a bar graph showing the number of MBP+ cells quantified in three independent experiments (mean±SD).
FIG. 6E illustrates the qRT-PCR of the transcript levels of the late differentiation marker MOG in treated cells.

The effects of 4c from 1 nM to 10 µM on the expression of differentiation markers in an immunocytochemical analysis was also studied. Specifically, proteoglycan NG2, recognized by antibodies, identifies progenitor cells, lipid sulfatides (i.e. O4+) label cells starting from an intermediate stage of maturation, and myelin basic protein (MBP) marks myelin-bearing cells (FIG. 6). In untreated cultures, the progression of progenitors to mature oligodendrocytes was characterized by the progressive loss of NG2 and the gradual acquisition of O4 immunoreactivity in 2-3 days and followed by the acquisition of a myelinating phenotype. The latter was characterized by the extension of myelin membranes recognized by O4 and MBP antibodies. A two-day treatment with 10 nM 4c promoted a shift towards the differentiated phenotype, as documented by an increased percentage of O4+ cells and a concomitant decrease of NG2+ progenitors (FIGS. 6A and 6B). The pro-differentiation effect of 10 nM 4c was confirmed by 4-day treatment of progenitor cultures, which showed increased percentage of MBP+ cells (FIGS. 6C and 6D) and increased transcript levels of the late-differentiation marker myelin oligodendrocyte glycoprotein (MOG), an important constituent of myelin (FIG. 6E). Therefore, this CBP inhibitor at very low doses appeared to push the progenitors towards a differentiative phenotype, whereas doses greater than 10 nM resulted in a bell-shaped curve of effects.

Figure 7:
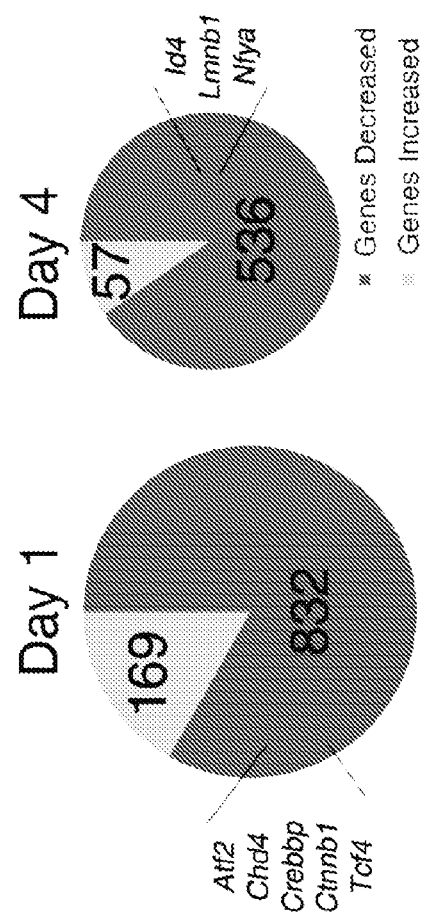
FIG. 7 is a pie-diagram representing genes that were down-regulated (dark) or up-regulated (light) in oligodendrocyte progenitor cultures treated with 4c for 1 day (left) or 4 days (right).
Figure 8:
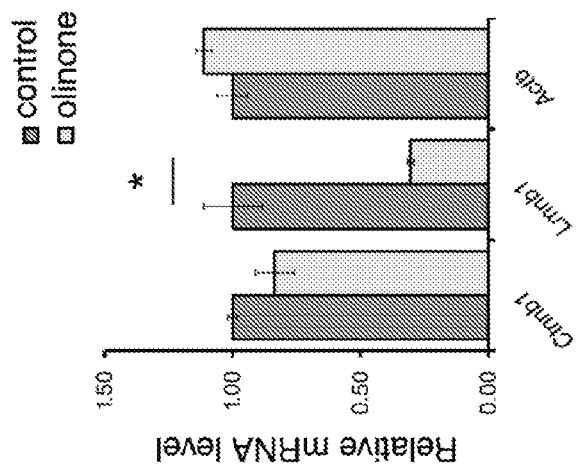
FIG. 8 shows the qRT-PCR of the transcript levels of Ctnnb1 and Lmnb1, two genes down-regulated during oligodendrocyte progenitor differentiation. Raw values were normalized to Gapdh levels and expressed relative to the levels detected in cells kept for 1 day in ODM. A housekeeping gene (act) was used as a control.
Figure 9:
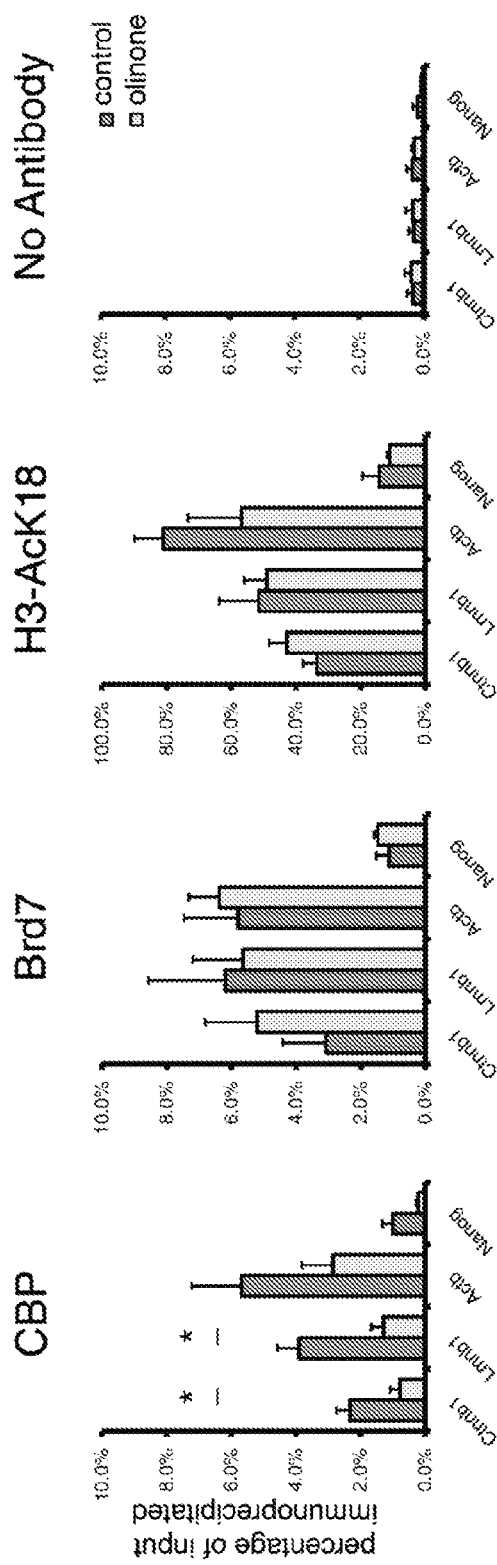
FIG. 9 illustrates the ChIP analysis of samples isolated from cells cultured as previously described and then precipitated using antibodies specific for CBP, and for H3K18ac. A mock ChIP (No Antibody) was used as negative control. The amount of chromatin recovered at the Lmnb1 transcription start site was measured by qPCR and expressed as percentage of input for each sample. Error bars are s.e.m. of three independent experiments (*p<0.05, **p<0.01 two-tail t test).

To determine how 4c exerts the pro-differentiative effect at 10 nM on the lineage progression of oligodendrocyte progenitors when the global histone acetylation is unchanged, a possibility that the compound would primarily affect CBP binding to target genes was investigated. To test this hypothesis, a microarray analysis was performed of cultures either untreated or treated with 10 nM 4c for 1 or 4 days. After one day of the treatment, 832 genes were decreased and 169 increased more than 1.2 fold; after four days, 536 genes remained down-regulated and 57 up-regulated (FIG. 7). Among the genes down-regulated by 4c treatment, several genes whose expression is decreased during progenitor differentiation, including beta-catenin (Ctnnb1), Id4, Nfya and lamin B1 (Lmnb1) were identified. The reduced expression of Ctnnb1 and Lmnb1 (FIG. 8) was validated in the 4c-treated cells, and detected decreased CBP occupancy at the promoters of these genes as assessed by chromatin immunoprecipitation (ChIP) (FIG. 9).

Quantitative ChIP analysis of these gene regulatory regions revealed that in cells treated for one day with 10 nM 4c, the association of CBP, but not the acetylation of histone H3 at lysine 18 (H3K18ac) was decreased in all the promoters analyzed. It has recently been reported that CBP functions as a transcriptional co-activator in Wnt/β-catenin signaling for transcriptional expression of Oct4 and Sox2 for the maintenance of murine embryonic stem cell pluripotency (Miyabayashi, T. et al. *Proc Natl Acad Sci USA* 104, 5668-73 (2007)) and blocking of Wnt/β-catenin signaling favors neuronal differentiation (Teo, J. L. et al., *Proc Natl Acad Sci USA* 102, 12171-6 (2005)). Taken together, these results suggest that 4c likely promotes the progression of progenitors towards a more mature phenotype by decreasing CBP via its bromodomain binding to the promoters of certain inhibitory genes resulting in their down-regulation during differentiation.

Figure 10:
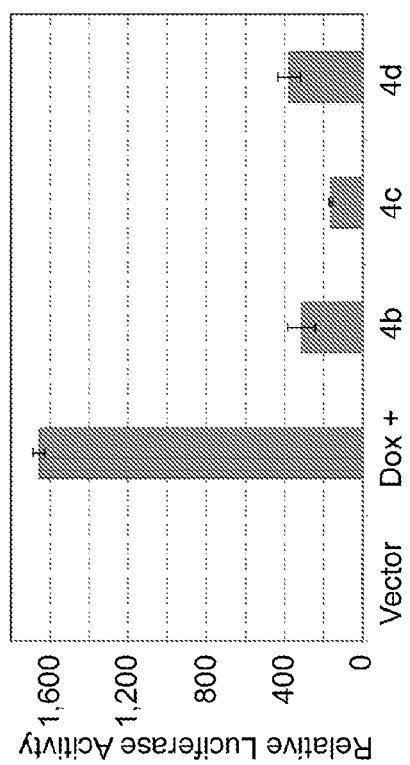
FIG. 10 shows the dose-dependent inhibition of p53-induced p21 luciferase activity in U2OS cells upon doxorubicin treatment in the presence of 4c (25 μM). The luciferase activity was normalized to renilla luciferase as a control. The $IC_{50}$ was calculated using PRISM software.

Example 10—Blocking Stress-Induced Transcriptional Activity of p53 by CBP BRD Inhibitors The activity of the pyrido-indole compounds (FIG. 10) were evaluated for their ability to inhibit p53 activation in human osteosarcoma (U2OS) cells. The p53 activation was induced by DNA damage upon treatment of doxorubicin, and effects of compound treatment were measured by p53-dependent p21 luciferase activity. U2OS Cells were transfected with p21 luciferase (1 µg) and *renilla luciferase* (100 ng) vectors in six-well plate format using Fugene 6 (Roche). 1.1 µg of vector was incubated with 3 mL of Fugene 6 reagent for 30 min. After 3-4 hours of transfection, cell were treated with compounds overnight, and then exposed to 300 ng of doxorubicin for the next 24 hours. In these experiments, DMSO, transfected cells with empty vectors, and cells without doxorubicin were used as controls. The DMSO concentration was maintained at 0.01%. Transfected cells with doxorubicin treatment were used as a positive control. The luciferase activity was estimated by following the manufacturer's instruction (Promega) in a luminometer. Both active and passive lysis of cells yielded consistent results. The inhibitory activity ($IC_{50}$) of a small molecule on p21 luciferase activity was obtained from the average of three biological replicates using PRISM software. As shown in FIG. 10B, compound 4c exhibited the most potent effect in inhibiting p53-induced p21 activation under doxorubicin treatment, which is consistent with in vitro structure-activity relationship studies of these chemical analogs in their ability to inhibit CBP bromodomain binding lysine-acetylated peptide, as determined by a fluorescence polarization assay (FIG. 1B).

Figure 12:
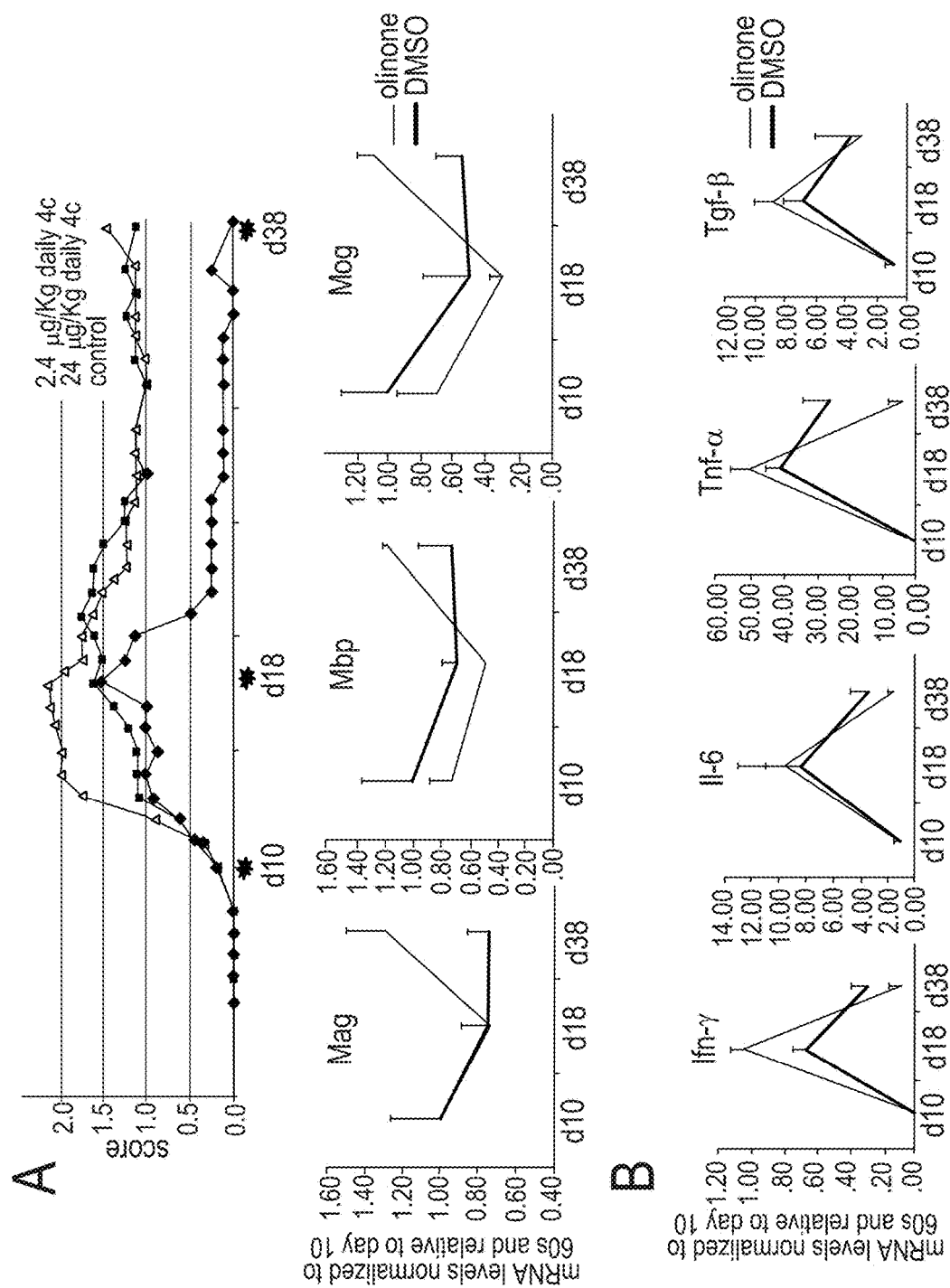
FIG. 12A illustrates a score graph of clinical severity of EAE in mice injected with MOG as described herein. Each group was composed of 6-9 mice. Below the score, the graphs show the levels of myelin transcripts detected at the times denoted by asterisks in the score graph. 12B provides transcript levels detected in the spinal cord of mice harvested at the same time points as the asterisks in 12A.

Example 11—Treatment with Nanomolar Concentrations of 4c Promotes Faster Recovery and Myelin Gene Expression in Mice with MOG-Induced EAE An in vivo mouse model study was conducted to determine how treatment with 4c would modulate oligodendrocyte progenitor differentiation and impact repair after demyelination. In a first series of experiments, a model of immune-mediated demyelination was used. EAE was induced by subcutaneous injection of 300 µg of MOG35-55 peptide thoroughly emulsified in complete Freund's adjuvant containing heat-inactivated *Mycobacterium tuberculosis* in the mouse flank on day 0 and 7. Pertussis toxin (500 ng) was intraperitoneally injected on day 0 and 2. After immunization mice were observed and weighed daily and scored for severity of symptoms as follows: 0, no detectable symptoms; 1, loss of tail tone; 2, hindlimb weakness or abnormal gait; 3, complete paralysis of the hindlimbs; 4, complete hindlimb and forelimb paralysis; 5, death. A minimum of 6-9 animals received daily intraperitoneal injections of 4c, starting from day 4 after immunization with the MOG peptide (FIG. 12A) and weight and clinical score were recorded daily. Disease onset was similar in mice treated with 4c compared to DMSO-injected controls. The similar onset of the disease suggested that at nanomolar concentrations 4c was not effective in blocking lymphocyte activation although it was effective in modulating gene expression in more sensitive cell types. At day 18, despite the similar levels of myelin and cytokine genes detected in the spinal cord of 4c-treated mice and in vehicle-injected controls, the 4c-treated group showed less severe disease (FIG. 12B and Table 3 below). A difference, however, was detected during the recovery period, that was dramatically accelerated in mice receiving 2.4 µg/Kg 4c compared to vehicle controls, and accompanied by a significant increase of myelin gene transcripts, in the presence of similar levels of cytokines (FIG. 12B).

One of the difficulties of such an experimental design was the fact that it is difficult to exclude the possibility that the faster recovery was due to decreased inflammation, rather than a direct enhancement of the repair potential of endogenous progenitors in the CNS. To address whether the effect of 2.4 µg/Kg 4c was due to its effect on the peripheral organs or the CNS, histones were extracted from lymphnodes and spinal cords at day 18 (i.e. peak of clinical symptoms) and at day 38 (the end of the recovery period).

TABLE 3

| Groups | Treatment | Number of animals with clinical signs | Maximum score | Average score | Number of mice with score <0.5 |
|---|---|---|---|---|---|
| Group 1 | 2.4 µg/kg (100 nM) | 5 out of 7 | 2.5/3 | 2.25 | 4/5 |
| Group 2 | 0.24 µg/kg (10 nM) | 4 out of 7 | 2.5 | 2.25 | 1/4 |
| Group 3 | DMSO | 6 out of 7 | 3 | 2.75 | 1/6 |

Figure 13:
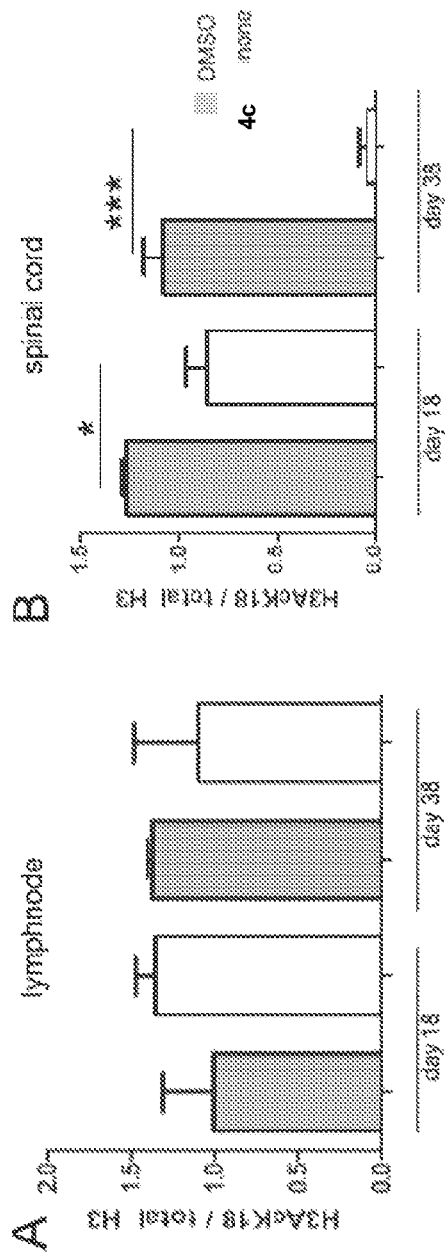
FIG. 13 shows histone acetylation in lymphnodes (A) and spinal cord (B) of 4c-treated mice. Quantification of western blots results. The bars show the ratio between acetyl-K18 H3/total H3 in vehicle-treated controls (gray) and 4c-treated mice (white).

These extracts were then processed for western blot for acetylated Lys 18 of histone H3 and total histone H3, the former of which is linked to gene transcriptional activation. The graphs in FIG. 13 show the effect of nanomolar 4c treatment on histone acetylation in the spinal cord (FIG. 13B), but not in the lymphnode (FIG. 13A). Together these results strongly suggest that 4c modulates histone deacetylation and favors myelin gene expression in the spinal cord, but not in lymphnodes when administer at nanomolar concentrations.

Figure 14:
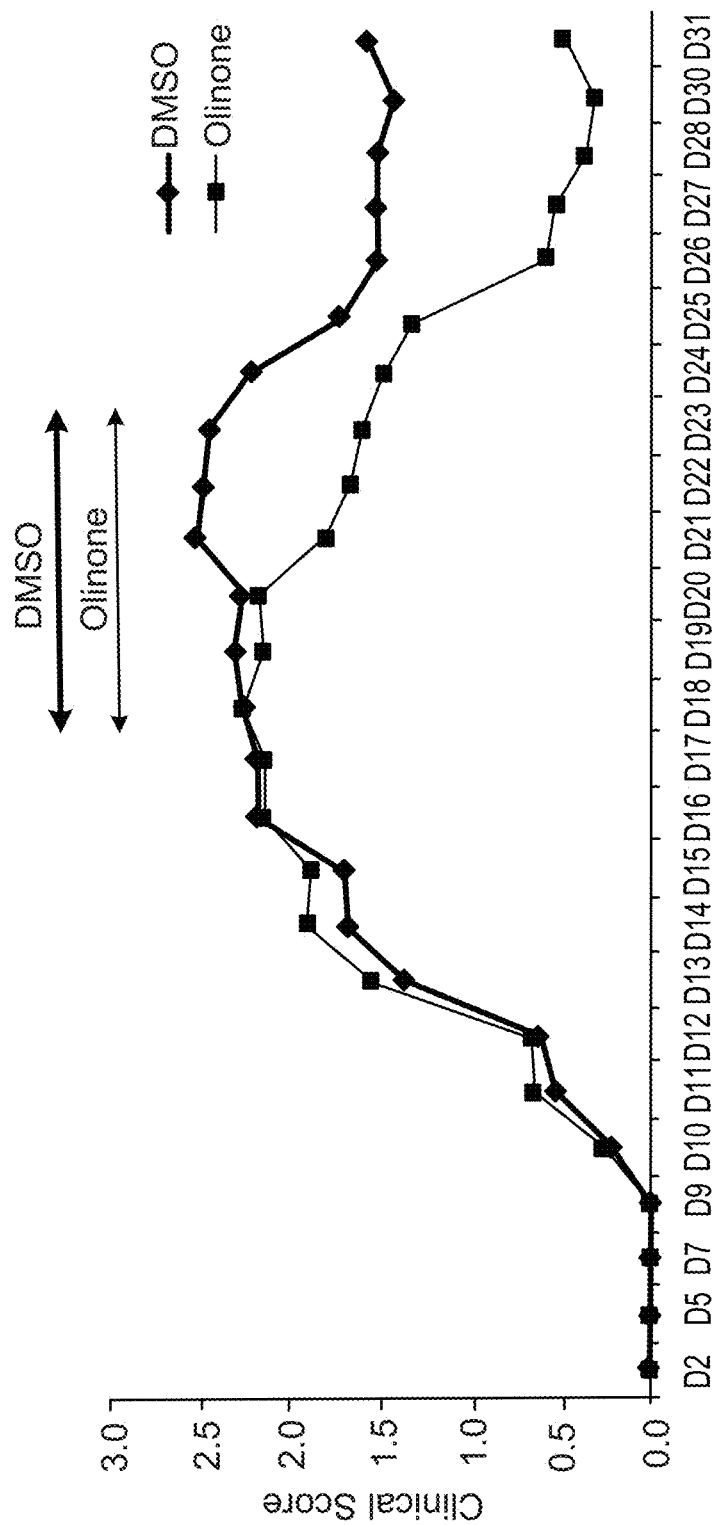
FIG. 14 illustrates seven-day 4c treatment accelerates recovery from MOG-induced EAE even if started AFTER the onset of clinical symptoms.

Example 12—Treatment with Nanomolar Concentrations of 4c is Effective in Promoting Repair Even when Started after Disease Onset in Two Models of Demyelination This study was conducted to determine whether the effectiveness of 4c can be observed in animals even if started once the disease has progressed to peak clinical symptoms. For this reason, MOG-dependent EAE in mice was induced and the animals scored daily. On day 18 post-immunization mice with a score of 2.5-3.0 (paralysis of one leg and weakness of the other to paralysis of both hindlimbs) were selected and divided into two groups receiving either 4c or vehicle treatment for 7 days. Remarkably, after 3-4 days of treatment, the two groups were distinguisable, since the 4c treated mice showed signs of recovery (FIG. 14).

Figure 15:
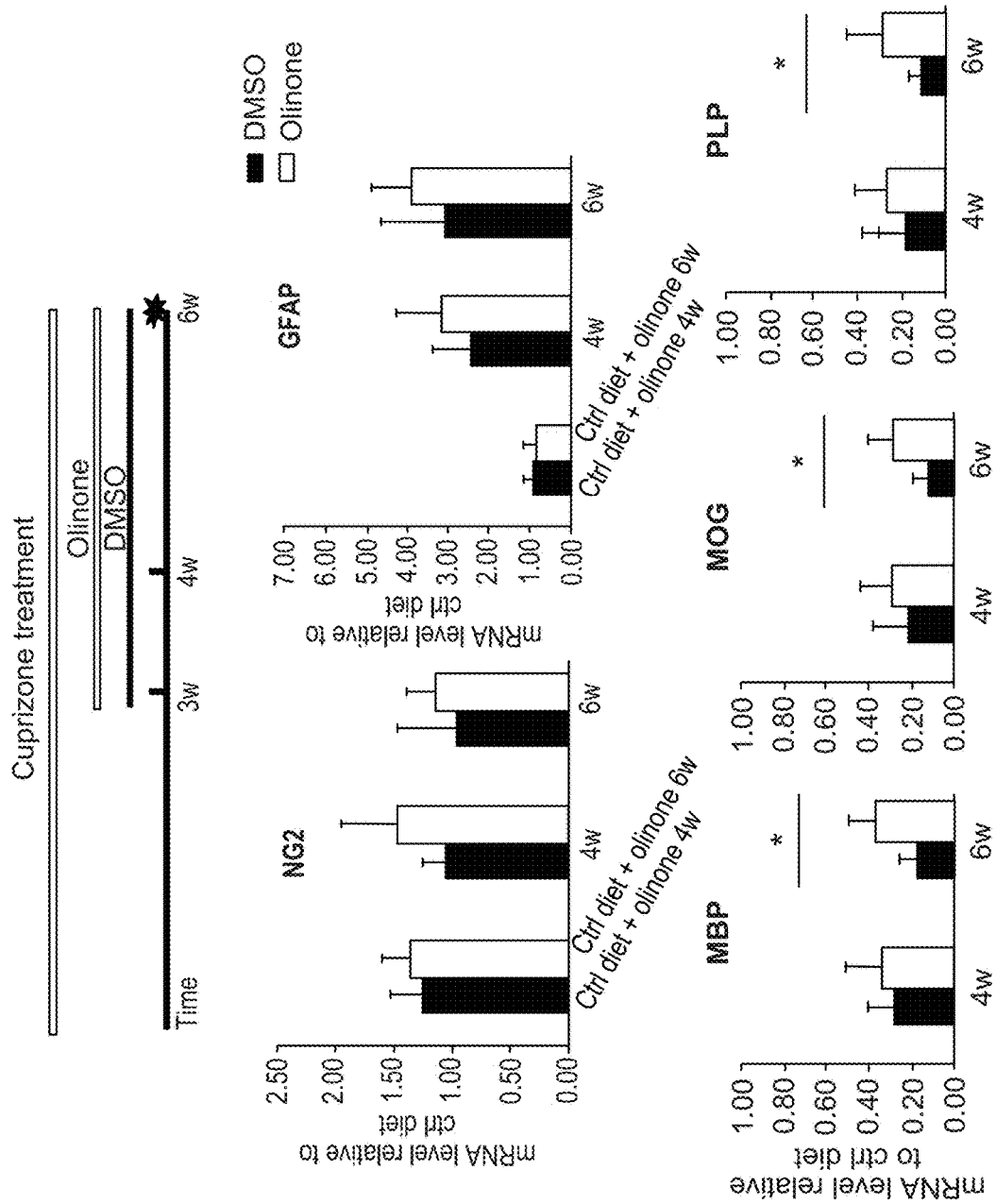
FIG. 15 shows 4c treatment increases myelin gene transcripts in old mice with cuprizone-induced demyelination. Effect of treatment with 2.4 μg/Kg 4c (olinone; red bars) and DMSO (black bars) treatment on the expression of progenitor (i.e. NG2), astrocytic (i.e. GFAP) and oligodendrocyte (i.e. MBP, MOG, PLP) genes.
Figure 16:
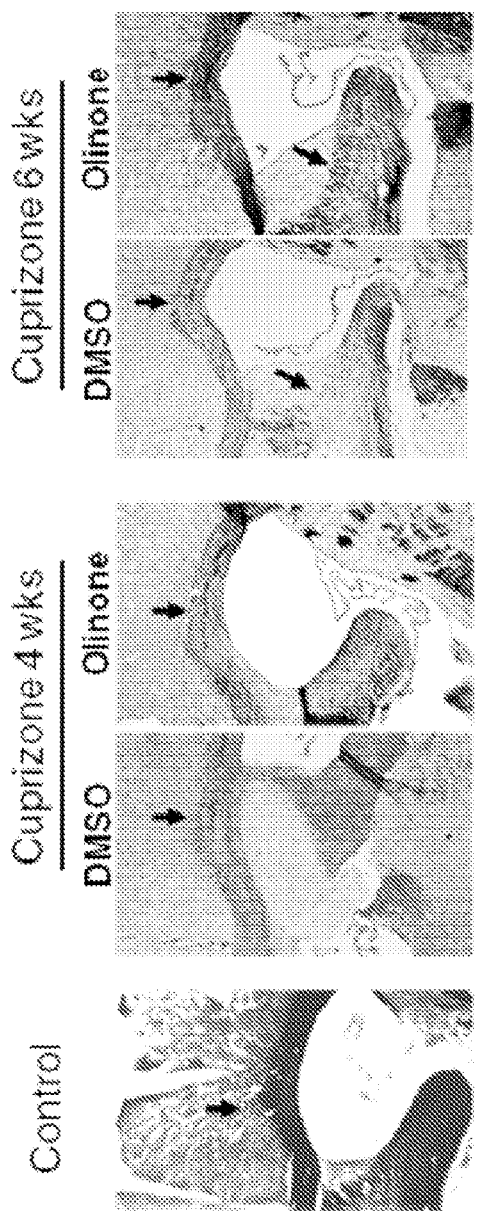
FIG. 16 illustrates enhanced remyelination in 4c-treated mice. Myelin staining in control (arrow) reveals a dark staining. Cuprizone damages myelin and this can be best seen as a decreased in the staining intensity. The effect on repair is shown by the darker intensity of the myelinated fibers.

A similar experiment was repeated in the cuprizone model of demyelination (FIG. 15). This model, characterized by precocious loss of myelin gene transcripts and oligodendrocyte apoptosis, followed by a repair phase characterized by expansion of the progenitor pool followed by differentiation has been previously described (Matsushima, G. K., and Morell, P. (2001). *Brain Pathol* 11:107-116). It was shown that in young mice the repair phase starts at week 3 and is characterized by the HDAC-dependent phase of differentiation of endogenous progenitors (Shen, S., Sandoval, J., Swiss, V. A., Li, J., Dupree, J., Franklin, R. J., and Casaccia-Bonnefil, P. (2008) *Nat Neurosci* 11:1024-1034) old mice repair was impaired, due to unopposed HAT activity, resulting in high levels of transcriptional inhibitors of oligodendrocyte differentiation and low myelin gene transcripts. 4c injection in old mice, starting during the $3^{rd}$ week, increased myelin gene transcripts (FIG. 15) and favors the formation of new myelin, as shown by eryochrome cyanine staining of myelinated fibers (FIG. 16). Taken together, these data identify 4c, a small molecule targeting the bromodomain of CBP/P300 as a promising therapeutic target for enhancing new myelin formation.

A number of embodiments of the invention have been described. Nevertheless, it will be understood that various modifications may be made without departing from the spirit and scope of the invention. Accordingly, other embodiments are within the scope of the following claims.

What is claimed is:

1. A compound of formula (1):

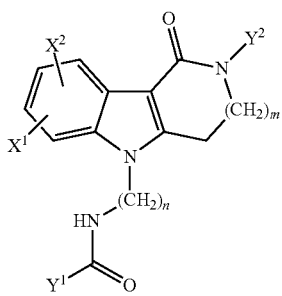

or a pharmaceutically acceptable salt form thereof, wherein:

$Y^1$ is selected from the group consisting of: H, $C_1$-$C_6$ alkyl, $C_1$-$C_6$ haloalkyl, halo, and $OR^3$;

$Y^2$ is selected from the group consisting of H, $C_1$-$C_6$ alkyl, $C_1$-$C_6$ haloalkyl, halo, and $OR^3$;

$X^1$ and $X^2$ are independently selected from the group consisting of: H, $C_1$-$C_6$ alkyl, $C_1$-$C_6$ haloalkyl, halo, —$NO_2$, —OH, —O($C_1$-$C_6$ alkyl), —O($C_1$-$C_6$ haloalkyl), —S($C_1$-$C_6$ alkyl), —$NR^1R^2$, —$NR^1$(C(O)$R^2$), —C(O)($C_1$-$C_6$ alkyl), —C(O)$OR^1$, —C(O)$NR^1R^2$, $C_5$-$C_{14}$ aryl, and $C_4$-$C_{14}$ heteroaryl;

each $R^1$ and $R^2$ are independently selected from H and $C_1$-$C_6$ alkyl;

each $R^3$ is independently selected from H, $C_1$-$C_6$ alkyl, and $C_5$-$C_{14}$ aryl;

n and m are independently integers from 1 to 6.

2. The compound of claim 1, wherein $Y^1$ is —$OR^3$ or $C_1$-$C_6$ alkyl.

3. The compound of claim 1, wherein $Y^1$ is —OH or —OPh.

4. The compound of claim 1, wherein $Y^1$ is $CH_3$ or $CH_2CH_3$.

5. The compound of claim 1, wherein $Y^2$ is selected from the group consisting of H, $C_1$-$C_6$ alkyl, and —$OR^3$.

6. The compound of claim 1, wherein $Y^2$ is H.

7. The compound of claim 1, wherein $X^1$ and $X^2$ are H.

8. The compound of claim 1, wherein the compound of formula (1) is selected from the group consisting of:

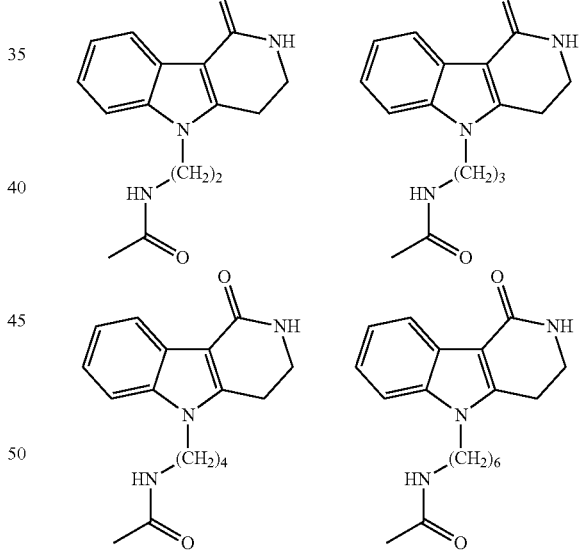

or a pharmaceutically acceptable salt form thereof.

9. A pharmaceutical composition comprising a compound of claim claim 1, or a pharmaceutically acceptable salt thereof, and a pharmaceutically acceptable excipient.

10. A method for ameliorating one or more symptoms of and/or ameliorating the underlying metabolic causes of symptoms of a neurological disorder in a patient where NF-kB is implicated in the pathology of the disorder, the method comprising administering a therapeutically effective amount of a compound of claim 1, or a pharmaceutically acceptable salt form thereof, to the patient.

* * * * *

SEQUENCE LISTING

<160> NUMBER OF SEQ ID NOS: 38

<210> SEQ ID NO 1
<211> LENGTH: 114
<212> TYPE: PRT
<213> ORGANISM: Artificial Sequence
<220> FEATURE:
<223> OTHER INFORMATION: synthetic peptide

<400> SEQUENCE: 1

Ile Phe Lys Pro Glu Glu Leu Arg Gln Ala Leu Met Pro Thr Leu Glu
1               5                   10                  15

Ala Leu Tyr Arg Gln Asp Pro Glu Ser Leu Pro Phe Arg Gln Pro Val
                20                  25                  30

Asp Pro Gln Leu Leu Gly Ile Pro Asp Tyr Phe Asp Ile Val Lys Asn
            35                  40                  45

Pro Met Asp Leu Ser Thr Ile Lys Arg Lys Leu Asp Thr Gly Gln Tyr
    50                  55                  60

Gln Glu Pro Trp Gln Tyr Val Asp Asp Val Trp Leu Met Phe Asn Asn
65                  70                  75                  80

Ala Trp Leu Tyr Asn Arg Lys Thr Ser Arg Val Tyr Lys Phe Cys Ser
                85                  90                  95

Lys Leu Ala Glu Val Phe Glu Gln Glu Ile Asp Pro Val Met Gln Ser
            100                 105                 110

Leu Gly

<210> SEQ ID NO 2
<211> LENGTH: 114
<212> TYPE: PRT
<213> ORGANISM: Artificial Sequence
<220> FEATURE:
<223> OTHER INFORMATION: synthetic peptide

<400> SEQUENCE: 2

Ile Phe Lys Pro Glu Glu Leu Arg Gln Ala Leu Met Pro Thr Leu Glu
1               5                   10                  15

Ala Leu Tyr Arg Gln Asp Pro Glu Ser Leu Pro Phe Arg Gln Pro Val
                20                  25                  30

Asp Pro Gln Leu Leu Gly Ile Pro Asp Tyr Phe Asp Ile Val Lys Ser
            35                  40                  45

Pro Met Asp Leu Ser Thr Ile Lys Arg Lys Leu Asp Thr Gly Gln Tyr
    50                  55                  60

Gln Glu Pro Trp Gln Tyr Val Asp Asp Ile Trp Leu Met Phe Asn Asn
65                  70                  75                  80

Ala Trp Leu Tyr Asn Arg Lys Thr Ser Arg Val Tyr Lys Tyr Cys Ser
                85                  90                  95

Lys Leu Ser Glu Val Phe Glu Gln Glu Ile Asp Pro Val Met Gln Ser
            100                 105                 110

Leu Gly

<210> SEQ ID NO 3
<211> LENGTH: 113
<212> TYPE: PRT
<213> ORGANISM: Artificial Sequence
<220> FEATURE:
<223> OTHER INFORMATION: synthetic peptide

<400> SEQUENCE: 3

Gly Arg Val Thr Asn Gln Leu Gln Tyr Leu His Lys Val Val Met Lys

-continued

```
               1               5                  10                 15
            Ala Leu Trp Lys His Gln Phe Ala Trp Pro Phe Arg Gln Pro Val Asp
                        20                  25                 30

Ala Val Lys Leu Gly Leu Pro Asp Tyr His Lys Ile Ile Lys Gln Pro
                        35                  40                 45

Met Asp Met Gly Thr Ile Lys Arg Arg Leu Glu Asn Asn Tyr Tyr Trp
                        50                  55                 60

Ala Ala Ser Glu Cys Met Gln Asp Phe Asn Thr Met Phe Thr Asn Cys
             65                 70                  75                 80

Tyr Ile Tyr Asn Lys Pro Thr Asp Asp Ile Val Leu Met Ala Gln Thr
                        85                  90                 95

Leu Glu Lys Ile Phe Leu Gln Lys Val Ala Ser Met Pro Gln Glu Glu
                        100                 105                110

Gln

<210> SEQ ID NO 4
<211> LENGTH: 113
<212> TYPE: PRT
<213> ORGANISM: Artificial Sequence
<220> FEATURE:
<223> OTHER INFORMATION: synthetic peptide

<400> SEQUENCE: 4

Gly Arg Lys Thr Asn Gln Leu Gln Tyr Met Gln Asn Val Val Val Lys
             1                  5                  10                 15

Thr Leu Trp Lys His Gln Phe Ala Trp Pro Phe Tyr Gln Pro Val Asp
                        20                  25                 30

Ala Ile Lys Leu Asn Leu Pro Asp Tyr His Lys Ile Ile Lys Asn Pro
                        35                  40                 45

Met Asp Met Gly Thr Ile Lys Lys Arg Leu Glu Asn Asn Tyr Tyr Trp
                        50                  55                 60

Ser Ala Ser Glu Cys Met Gln Asp Phe Asn Thr Met Phe Thr Asn Cys
             65                 70                  75                 80

Tyr Ile Tyr Asn Lys Pro Thr Asp Asp Ile Val Leu Met Ala Gln Ala
                        85                  90                 95

Leu Glu Lys Ile Phe Leu Gln Lys Val Ala Gln Met Pro Gln Glu Glu
                        100                 105                110

Val

<210> SEQ ID NO 5
<211> LENGTH: 113
<212> TYPE: PRT
<213> ORGANISM: Artificial Sequence
<220> FEATURE:
<223> OTHER INFORMATION: synthetic peptide

<400> SEQUENCE: 5

Lys Arg Gln Thr Asn Gln Leu Gln Tyr Leu Leu Arg Val Val Leu Lys
             1                  5                  10                 15

Thr Leu Trp Lys His Gln Phe Ala Trp Pro Phe Gln Gln Pro Val Asp
                        20                  25                 30

Ala Val Lys Leu Asn Leu Pro Asp Tyr Lys Ile Ile Lys Thr Pro
                        35                  40                 45

Met Asp Met Gly Thr Ile Lys Lys Arg Leu Glu Asn Asn Tyr Tyr Trp
                        50                  55                 60

Asn Ala Gln Glu Cys Ile Gln Asp Phe Asn Thr Met Phe Thr Asn Cys
             65                 70                  75                 80
```

-continued

```
Tyr Ile Tyr Asn Lys Pro Gly Asp Asp Ile Val Leu Met Ala Glu Ala
                85                  90                  95

Leu Glu Lys Leu Phe Leu Gln Lys Ile Asn Glu Leu Pro Thr Glu Glu
            100                 105                 110

Thr

<210> SEQ ID NO 6
<211> LENGTH: 113
<212> TYPE: PRT
<213> ORGANISM: Artificial Sequence
<220> FEATURE:
<223> OTHER INFORMATION: synthetic peptide

<400> SEQUENCE: 6

Gly Arg Leu Thr Asn Gln Leu Gln Tyr Leu Gln Lys Val Val Leu Lys
1               5                   10                  15

Asp Leu Trp Lys His Ser Phe Ser Trp Pro Phe Gln Arg Pro Val Asp
            20                  25                  30

Ala Val Lys Leu Gln Leu Pro Asp Tyr Tyr Thr Ile Ile Lys Asn Pro
        35                  40                  45

Met Asp Leu Asn Thr Ile Lys Lys Arg Leu Glu Asn Lys Tyr Tyr Ala
50                  55                  60

Lys Ala Ser Glu Cys Ile Glu Asp Phe Asn Thr Met Phe Ser Asn Cys
65                  70                  75                  80

Tyr Leu Tyr Asn Lys Pro Gly Asp Asp Ile Val Leu Met Ala Gln Ala
                85                  90                  95

Leu Glu Lys Leu Phe Met Gln Lys Leu Ser Gln Met Pro Gln Glu Glu
            100                 105                 110

Gln

<210> SEQ ID NO 7
<211> LENGTH: 115
<212> TYPE: PRT
<213> ORGANISM: Artificial Sequence
<220> FEATURE:
<223> OTHER INFORMATION: synthetic peptide

<400> SEQUENCE: 7

Gly Lys Leu Ser Glu Gln Leu Lys His Cys Asn Gly Ile Leu Lys Glu
1               5                   10                  15

Leu Leu Ser Lys Lys His Ala Ala Tyr Ala Trp Pro Phe Tyr Lys Pro
            20                  25                  30

Val Asp Ala Ser Ala Leu Gly Leu His Asp Tyr His Asp Ile Ile Lys
        35                  40                  45

His Pro Met Asp Leu Ser Thr Val Lys Arg Lys Met Glu Asn Arg Asp
50                  55                  60

Tyr Arg Asp Ala Gln Glu Phe Ala Ala Asp Val Arg Leu Met Phe Ser
65                  70                  75                  80

Asn Cys Tyr Lys Tyr Asn Pro Pro Asp His Asp Val Val Ala Met Ala
                85                  90                  95

Arg Lys Leu Gln Asp Val Phe Glu Phe Arg Tyr Ala Lys Met Pro Asp
            100                 105                 110

Glu Pro Leu
        115

<210> SEQ ID NO 8
<211> LENGTH: 115
```

```
<212> TYPE: PRT
<213> ORGANISM: Artificial Sequence
<220> FEATURE:
<223> OTHER INFORMATION: synthetic peptide

<400> SEQUENCE: 8

Gly Lys Leu Ser Glu His Leu Arg Tyr Cys Asp Ser Ile Leu Arg Glu
1               5                   10                  15

Met Leu Ser Lys Lys His Ala Ala Tyr Ala Trp Pro Phe Tyr Lys Pro
                20                  25                  30

Val Asp Ala Glu Ala Leu Glu Leu His Asp Tyr His Asp Ile Ile Lys
            35                  40                  45

His Pro Met Asp Leu Ser Thr Val Lys Arg Lys Met Asp Gly Arg Glu
        50                  55                  60

Tyr Pro Asp Ala Gln Gly Phe Ala Ala Asp Val Arg Leu Met Phe Ser
65                  70                  75                  80

Asn Cys Tyr Lys Tyr Asn Pro Pro Asp His Glu Val Val Ala Met Ala
                85                  90                  95

Arg Lys Leu Gln Asp Val Phe Glu Met Arg Phe Ala Lys Met Pro Asp
            100                 105                 110

Glu Pro Val
        115

<210> SEQ ID NO 9
<211> LENGTH: 115
<212> TYPE: PRT
<213> ORGANISM: Artificial Sequence
<220> FEATURE:
<223> OTHER INFORMATION: synthetic peptide

<400> SEQUENCE: 9

Ser Lys Val Ser Glu Gln Leu Lys Cys Cys Ser Gly Ile Leu Lys Glu
1               5                   10                  15

Met Phe Ala Lys Lys His Ala Ala Tyr Ala Trp Pro Phe Tyr Lys Pro
                20                  25                  30

Val Asp Val Glu Ala Leu Gly Leu His Asp Tyr Cys Asp Ile Ile Lys
            35                  40                  45

His Pro Met Asp Met Ser Thr Ile Lys Ser Lys Leu Glu Ala Arg Glu
        50                  55                  60

Tyr Arg Asp Ala Gln Glu Phe Gly Ala Asp Val Arg Leu Met Phe Ser
65                  70                  75                  80

Asn Cys Tyr Lys Tyr Asn Pro Pro Asp His Glu Val Val Ala Met Ala
                85                  90                  95

Arg Lys Leu Gln Asp Val Phe Glu Met Arg Phe Ala Lys Met Pro Asp
            100                 105                 110

Glu Pro Glu
        115

<210> SEQ ID NO 10
<211> LENGTH: 113
<212> TYPE: PRT
<213> ORGANISM: Artificial Sequence
<220> FEATURE:
<223> OTHER INFORMATION: synthetic peptide

<400> SEQUENCE: 10

Thr Phe Arg Glu Leu Arg Ile Phe Leu Arg Asn Val Thr His Arg Leu
1               5                   10                  15

Ala Ile Asp Lys Arg Phe Arg Val Phe Thr Lys Pro Val Asp Pro Asp
```

```
                20                  25                  30

Glu Val Pro Asp Tyr Val Thr Val Ile Lys Gln Pro Met Asp Leu Ser
                35                  40                  45

Ser Val Ile Ser Lys Ile Asp Leu His Lys Tyr Leu Thr Val Lys Asp
                50                  55                  60

Tyr Leu Arg Asp Ile Asp Leu Ile Cys Ser Asn Ala Leu Glu Tyr Asn
 65                  70                  75                  80

Pro Asp Arg Asp Pro Gly Asp Arg Leu Ile Arg His Arg Ala Cys Ala
                    85                  90                  95

Leu Arg Asp Thr Ala Tyr Ala Ile Ile Lys Glu Glu Leu Asp Glu Asp
                    100                 105                 110

Phe

<210> SEQ ID NO 11
<211> LENGTH: 114
<212> TYPE: PRT
<213> ORGANISM: Artificial Sequence
<220> FEATURE:
<223> OTHER INFORMATION: synthetic peptide

<400> SEQUENCE: 11

Asn Thr Leu Arg Glu Leu Arg Leu Phe Leu Arg Asp Val Thr Lys Arg
 1               5                   10                  15

Leu Ala Thr Asp Lys Arg Phe Asn Ile Phe Ser Lys Pro Val Ser Val
                20                  25                  30

Asp Ile Glu Glu Asp Tyr Leu Glu Val Ile Lys Glu Pro Met Asp Leu
                35                  40                  45

Ser Thr Val Ile Thr Lys Ile Asp Lys His Asn Tyr Leu Thr Ala Lys
                50                  55                  60

Asp Phe Leu Lys Asp Ile Asp Leu Ile Cys Ser Asn Ala Leu Glu Tyr
 65                  70                  75                  80

Asn Pro Asp Lys Asp Pro Gly Asp Lys Ile Ile Arg His Arg Ala Cys
                    85                  90                  95

Thr Leu Lys Asp Thr Ala His Ala Ile Ile Ala Ala Glu Leu Asp Pro
                    100                 105                 110

Glu Phe

<210> SEQ ID NO 12
<211> LENGTH: 110
<212> TYPE: PRT
<213> ORGANISM: Artificial Sequence
<220> FEATURE:
<223> OTHER INFORMATION: synthetic peptide

<400> SEQUENCE: 12

Val Glu Gln Thr Pro Leu Gln Glu Ala Leu Asn Gln Leu Met Arg Gln
 1               5                   10                  15

Leu Gln Arg Lys Asp Pro Ser Ala Phe Phe Ser Phe Pro Val Thr Asp
                20                  25                  30

Phe Ile Ala Pro Gly Tyr Ser Met Ile Ile Lys His Pro Met Asp Phe
                35                  40                  45

Ser Thr Met Lys Glu Lys Ile Lys Asn Asn Asp Tyr Gln Ser Ile Glu
                50                  55                  60

Glu Leu Lys Asp Asn Phe Lys Leu Met Cys Thr Asn Ala Met Ile Tyr
 65                  70                  75                  80

Asn Lys Pro Glu Thr Ile Tyr Tyr Lys Ala Ala Lys Lys Leu Leu His
                    85                  90                  95
```

```
Ser Gly Met Lys Ile Leu Ser Gln Glu Arg Ile Gln Ser Leu
        100                 105                 110

<210> SEQ ID NO 13
<211> LENGTH: 110
<212> TYPE: PRT
<213> ORGANISM: Artificial Sequence
<220> FEATURE:
<223> OTHER INFORMATION: synthetic peptide

<400> SEQUENCE: 13

Asn Glu Ser Thr Pro Ile Gln Gln Leu Leu Glu His Phe Leu Arg Gln
  1               5                  10                  15

Leu Gln Arg Lys Asp Pro His Gly Phe Phe Ala Phe Pro Val Thr Asp
                 20                  25                  30

Ala Ile Ala Pro Gly Tyr Ser Met Ile Ile Lys His Pro Met Asp Phe
             35                  40                  45

Gly Thr Met Lys Asp Lys Ile Val Ala Asn Glu Tyr Lys Ser Val Thr
         50                  55                  60

Glu Phe Lys Ala Asp Phe Lys Leu Met Cys Asp Asn Ala Met Thr Tyr
 65                  70                  75                  80

Asn Arg Pro Asp Thr Val Tyr Tyr Lys Leu Ala Lys Lys Ile Leu His
                 85                  90                  95

Ala Gly Phe Lys Met Met Ser Lys Glu Arg Leu Leu Ala Leu
            100                 105                 110

<210> SEQ ID NO 14
<211> LENGTH: 110
<212> TYPE: PRT
<213> ORGANISM: Artificial Sequence
<220> FEATURE:
<223> OTHER INFORMATION: synthetic peptide

<400> SEQUENCE: 14

Met Gln Leu Thr Pro Phe Leu Ile Leu Leu Arg Lys Thr Leu Glu Gln
  1               5                  10                  15

Leu Gln Glu Lys Asp Thr Gly Asn Ile Phe Ser Glu Pro Val Pro Leu
                 20                  25                  30

Ser Glu Val Pro Asp Tyr Leu Asp His Ile Lys Lys Pro Met Asp Phe
             35                  40                  45

Phe Thr Met Lys Gln Asn Leu Glu Ala Tyr Arg Tyr Leu Asn Phe Asp
         50                  55                  60

Asp Phe Glu Glu Asp Phe Asn Leu Ile Val Ser Asn Cys Leu Lys Tyr
 65                  70                  75                  80

Asn Ala Lys Asp Thr Ile Phe Tyr Arg Ala Ala Val Arg Leu Arg Glu
                 85                  90                  95

Gln Gly Gly Ala Val Leu Arg Gln Ala Arg Arg Gln Ala Glu
            100                 105                 110

<210> SEQ ID NO 15
<211> LENGTH: 111
<212> TYPE: PRT
<213> ORGANISM: Artificial Sequence
<220> FEATURE:
<223> OTHER INFORMATION: synthetic peptide

<400> SEQUENCE: 15

Lys Leu Thr Pro Ile Asp Lys Arg Lys Cys Glu Arg Leu Leu Leu Phe
  1               5                  10                  15
```

-continued

```
Leu Tyr Cys His Glu Met Ser Leu Ala Phe Gln Asp Pro Val Pro Leu
                 20                  25                  30

Thr Val Pro Asp Tyr Tyr Lys Ile Ile Lys Asn Pro Met Asp Leu Ser
             35                  40                  45

Thr Ile Lys Lys Arg Leu Gln Glu Asp Tyr Ser Met Tyr Ser Lys Pro
         50                  55                  60

Glu Asp Phe Val Ala Asp Phe Arg Leu Ile Phe Gln Asn Cys Ala Glu
 65                  70                  75                  80

Phe Asn Glu Pro Asp Ser Glu Val Ala Asn Ala Gly Ile Lys Leu Glu
                 85                  90                  95

Asn Tyr Phe Glu Glu Leu Leu Lys Asn Leu Tyr Pro Glu Lys Arg
            100                 105                 110
```

<210> SEQ ID NO 16
<211> LENGTH: 110
<212> TYPE: PRT
<213> ORGANISM: Artificial Sequence
<220> FEATURE:
<223> OTHER INFORMATION: synthetic peptide

<400> SEQUENCE: 16

```
Lys Leu Ser Pro Ala Asn Gln Arg Lys Cys Glu Arg Val Leu Leu Ala
 1               5                  10                  15

Leu Phe Cys His Glu Pro Cys Arg Pro Leu His Gln Leu Ala Thr Asp
                 20                  25                  30

Ser Thr Phe Ser Leu Asp Gln Pro Gly Gly Thr Leu Asp Leu Thr Leu
             35                  40                  45

Ile Arg Ala Arg Leu Gln Glu Lys Leu Ser Pro Pro Tyr Ser Ser Pro
         50                  55                  60

Gln Glu Phe Ala Gln Asp Val Gly Arg Met Phe Lys Gln Phe Asn Lys
 65                  70                  75                  80

Leu Thr Glu Asp Lys Ala Asp Val Gln Ser Ile Ile Gly Leu Gln Arg
                 85                  90                  95

Phe Phe Glu Thr Arg Met Asn Glu Ala Phe Gly Asp Thr Lys
            100                 105                 110
```

<210> SEQ ID NO 17
<211> LENGTH: 109
<212> TYPE: PRT
<213> ORGANISM: Artificial Sequence
<220> FEATURE:
<223> OTHER INFORMATION: synthetic peptide

<400> SEQUENCE: 17

```
Arg Asp Asp Ser Lys Asp Leu Ala Leu Cys Ser Met Ile Leu Thr Glu
 1               5                  10                  15

Met Glu Thr His Glu Asp Ala Trp Pro Phe Leu Leu Pro Val Asn Leu
                 20                  25                  30

Lys Leu Val Pro Gly Tyr Lys Lys Val Ile Lys Lys Pro Met Asp Phe
             35                  40                  45

Ser Thr Ile Arg Glu Lys Leu Ser Ser Gly Gln Tyr Pro Asn Leu Glu
         50                  55                  60

Thr Phe Ala Leu Asp Val Arg Leu Val Phe Asp Asn Cys Glu Thr Phe
 65                  70                  75                  80

Asn Glu Asp Asp Ser Asp Ile Gly Arg Ala Gly His Asn Met Arg Lys
                 85                  90                  95

Tyr Phe Glu Lys Lys Trp Thr Asp Thr Phe Lys Val Ser
            100                 105
```

```
<210> SEQ ID NO 18
<211> LENGTH: 110
<212> TYPE: PRT
<213> ORGANISM: Artificial Sequence
<220> FEATURE:
<223> OTHER INFORMATION: synthetic peptide

<400> SEQUENCE: 18

Lys Asp Pro Asp Gln Leu Tyr Thr Thr Leu Lys Asn Leu Leu Ala Gln
1               5                   10                  15

Ile Lys Ser His Pro Ser Ala Trp Pro Phe Met Glu Pro Val Lys Lys
            20                  25                  30

Ser Glu Ala Pro Asp Tyr Tyr Glu Val Ile Arg Phe Pro Ile Asp Leu
        35                  40                  45

Lys Thr Met Thr Glu Arg Leu Arg Ser Arg Tyr Tyr Val Thr Arg Lys
50                  55                  60

Leu Phe Val Ala Asp Leu Gln Arg Val Ile Ala Asn Cys Arg Glu Tyr
65                  70                  75                  80

Asn Pro Pro Asp Ser Glu Tyr Cys Arg Cys Ala Ser Ala Leu Glu Lys
                85                  90                  95

Phe Phe Tyr Phe Lys Leu Lys Glu Gly Gly Leu Ile Asp Lys
            100                 105                 110

<210> SEQ ID NO 19
<211> LENGTH: 110
<212> TYPE: PRT
<213> ORGANISM: Artificial Sequence
<220> FEATURE:
<223> OTHER INFORMATION: synthetic peptide

<400> SEQUENCE: 19

Arg Asp Pro Asp Gln Leu Tyr Ser Thr Leu Lys Ser Ile Leu Gln Gln
1               5                   10                  15

Val Lys Ser His Gln Ser Ala Trp Pro Phe Met Glu Pro Val Lys Arg
            20                  25                  30

Thr Glu Ala Pro Gly Tyr Tyr Glu Val Ile Arg Phe Pro Met Asp Leu
        35                  40                  45

Lys Thr Met Ser Glu Arg Leu Lys Asn Arg Tyr Tyr Val Ser Lys Lys
50                  55                  60

Leu Phe Met Ala Asp Leu Gln Arg Val Phe Thr Asn Cys Lys Glu Tyr
65                  70                  75                  80

Asn Pro Pro Glu Ser Glu Tyr Tyr Lys Cys Ala Asn Ile Leu Glu Lys
                85                  90                  95

Phe Phe Phe Ser Lys Ile Lys Glu Ala Gly Leu Ile Asp Lys
            100                 105                 110

<210> SEQ ID NO 20
<211> LENGTH: 110
<212> TYPE: PRT
<213> ORGANISM: Artificial Sequence
<220> FEATURE:
<223> OTHER INFORMATION: synthetic peptide

<400> SEQUENCE: 20

Pro Leu Thr Glu Lys Asp Tyr Glu Gly Leu Lys Arg Val Leu Arg Ser
1               5                   10                  15

Leu Gln Ala His Lys Met Ala Trp Pro Phe Leu Glu Pro Val Asp Pro
            20                  25                  30
```

-continued

Asn Asp Ala Pro Asp Tyr Tyr Gly Val Ile Lys Glu Pro Met Asp Leu
         35                  40                  45

Ala Thr Met Glu Glu Arg Val Gln Arg Arg Tyr Tyr Glu Lys Leu Thr
 50                  55                  60

Glu Phe Val Ala Asp Met Thr Lys Ile Phe Asp Asn Cys Arg Tyr Tyr
 65                  70                  75                  80

Asn Pro Ser Asp Ser Pro Phe Tyr Gln Cys Ala Glu Val Leu Glu Ser
                 85                  90                  95

Phe Phe Val Gln Lys Leu Lys Gly Phe Lys Ala Ser Arg Ser
                100                 105                 110

<210> SEQ ID NO 21
<211> LENGTH: 111
<212> TYPE: PRT
<213> ORGANISM: Artificial Sequence
<220> FEATURE:
<223> OTHER INFORMATION: synthetic peptide

<400> SEQUENCE: 21

Asp Asp Gln Val Ala Phe Ser Phe Ile Leu Asp Asn Ile Val Thr Gln
 1                5                  10                  15

Lys Met Met Ala Val Pro Asp Ser Trp Pro Phe His His Pro Val Asn
                 20                  25                  30

Lys Lys Phe Val Pro Asp Tyr Tyr Lys Val Ile Val Asn Pro Met Asp
                 35                  40                  45

Leu Glu Thr Ile Arg Lys Asn Ile Ser Lys His Lys Tyr Gln Ser Arg
 50                  55                  60

Glu Ser Phe Leu Asp Asp Val Asn Leu Ile Leu Ala Asn Ser Val Lys
 65                  70                  75                  80

Tyr Asn Gly Pro Glu Ser Gln Tyr Thr Lys Thr Ala Gln Glu Ile Val
                 85                  90                  95

Asn Val Cys Tyr Gln Thr Leu Thr Glu Tyr Asp Glu His Leu Thr
                100                 105                 110

<210> SEQ ID NO 22
<211> LENGTH: 111
<212> TYPE: PRT
<213> ORGANISM: Artificial Sequence
<220> FEATURE:
<223> OTHER INFORMATION: synthetic peptide

<400> SEQUENCE: 22

Asp Asp Gln Val Ala Phe Ser Phe Ile Leu Asp Asn Ile Val Thr Gln
 1                5                  10                  15

Lys Met Met Ala Val Pro Asp Ser Trp Pro Phe His His Pro Val Asn
                 20                  25                  30

Lys Lys Phe Val Pro Asp Tyr Tyr Lys Met Ile Val Asn Pro Val Asp
                 35                  40                  45

Leu Glu Thr Ile Arg Lys Asn Ile Ser Lys His Lys Tyr Gln Ser Arg
 50                  55                  60

Glu Ser Phe Leu Asp Asp Val Asn Leu Ile Leu Ala Asn Ser Val Lys
 65                  70                  75                  80

Tyr Asn Gly Pro Glu Ser Gln Tyr Thr Lys Thr Ala Gln Glu Ile Val
                 85                  90                  95

Asn Ile Cys Tyr Gln Thr Ile Thr Glu Tyr Asp Glu His Leu Thr
                100                 105                 110

<210> SEQ ID NO 23

```
<211> LENGTH: 110
<212> TYPE: PRT
<213> ORGANISM: Artificial Sequence
<220> FEATURE:
<223> OTHER INFORMATION: synthetic peptide

<400> SEQUENCE: 23

Asp Pro Met Val Thr Leu Ser Ser Ile Leu Glu Ser Ile Ile Asn Asp
1               5                   10                  15
Met Arg Asp Leu Pro Asn Thr Tyr Pro Phe His Thr Pro Val Asn Ala
            20                  25                  30
Lys Val Val Lys Asp Tyr Tyr Lys Ile Ile Thr Arg Pro Met Asp Leu
        35                  40                  45
Gln Thr Leu Arg Glu Asn Val Arg Lys Arg Leu Tyr Pro Ser Arg Glu
    50                  55                  60
Glu Phe Arg Glu His Leu Glu Leu Ile Val Lys Asn Ser Ala Thr Tyr
65                  70                  75                  80
Asn Gly Pro Lys His Ser Leu Thr Gln Ile Ser Gln Ser Met Leu Asp
                85                  90                  95
Leu Cys Asp Glu Lys Leu Lys Glu Lys Glu Asp Lys Leu Ala
            100                 105                 110

<210> SEQ ID NO 24
<211> LENGTH: 113
<212> TYPE: PRT
<213> ORGANISM: Artificial Sequence
<220> FEATURE:
<223> OTHER INFORMATION: synthetic peptide

<400> SEQUENCE: 24

Asn Leu Thr Lys Lys Met Lys Lys Ile Val Asp Ala Val Ile Lys Tyr
1               5                   10                  15
Lys Asp Ser Ser Ser Gly Arg Gln Leu Ser Glu Val Phe Ile Gln Leu
            20                  25                  30
Pro Ser Arg Lys Glu Leu Pro Glu Tyr Tyr Glu Leu Ile Arg Lys Pro
        35                  40                  45
Val Asp Phe Lys Lys Ile Lys Glu Arg Ile Arg Asn His Lys Tyr Arg
    50                  55                  60
Ser Leu Asn Asp Leu Glu Lys Asp Val Met Leu Leu Cys Gln Asn Ala
65                  70                  75                  80
Gln Thr Phe Asn Leu Glu Gly Ser Leu Ile Tyr Glu Asp Ser Ile Val
                85                  90                  95
Leu Gln Ser Val Phe Thr Ser Val Arg Gln Lys Ile Glu Lys Glu Asp
            100                 105                 110
Asp

<210> SEQ ID NO 25
<211> LENGTH: 109
<212> TYPE: PRT
<213> ORGANISM: Artificial Sequence
<220> FEATURE:
<223> OTHER INFORMATION: synthetic peptide

<400> SEQUENCE: 25

Lys Leu Thr Lys Gln Met Asn Ala Ile Ile Asp Thr Val Ile Asn Tyr
1               5                   10                  15
Lys Asp Arg Gln Leu Ser Glu Val Phe Ile Gln Leu Pro Ser Arg Lys
            20                  25                  30
Glu Leu Pro Glu Tyr Tyr Glu Leu Ile Arg Lys Pro Val Asp Phe Lys
```

```
            35                  40                  45
Lys Ile Lys Glu Arg Ile Arg Asn His Lys Tyr Arg Ser Leu Gly Asp
        50                  55                  60
Leu Glu Lys Asp Val Met Leu Leu Cys His Asn Ala Gln Thr Phe Asn
65                  70                  75                  80
Leu Glu Gly Ser Gln Ile Tyr Glu Asp Ser Ile Val Leu Gln Ser Val
                85                  90                  95
Phe Lys Ser Ala Arg Gln Lys Ile Ala Lys Glu Glu Glu
            100                 105
```

<210> SEQ ID NO 26
<211> LENGTH: 112
<212> TYPE: PRT
<213> ORGANISM: Artificial Sequence
<220> FEATURE:
<223> OTHER INFORMATION: synthetic peptide

<400> SEQUENCE: 26

```
Pro Met Gln Gln Lys Leu Asn Glu Val Tyr Glu Ala Val Lys Asn Tyr
1               5                   10                  15
Thr Asp Lys Arg Gly Arg Arg Leu Ser Ala Ile Phe Leu Arg Leu Pro
            20                  25                  30
Ser Arg Ser Glu Leu Pro Asp Tyr Tyr Leu Thr Ile Lys Lys Pro Met
        35                  40                  45
Asp Met Glu Lys Ile Arg Ser His Met Met Ala Asn Lys Tyr Gln Asp
    50                  55                  60
Ile Asp Ser Met Val Glu Asp Phe Val Met Met Phe Asn Asn Ala Cys
65                  70                  75                  80
Thr Tyr Asn Glu Pro Glu Ser Leu Ile Tyr Lys Asp Ala Leu Val Leu
                85                  90                  95
His Lys Val Leu Leu Glu Thr Arg Arg Asp Leu Glu Gly Asp Glu Asp
            100                 105                 110
```

<210> SEQ ID NO 27
<211> LENGTH: 112
<212> TYPE: PRT
<213> ORGANISM: Artificial Sequence
<220> FEATURE:
<223> OTHER INFORMATION: synthetic peptide

<400> SEQUENCE: 27

```
Tyr Leu Lys Glu Ile Leu Glu Gln Leu Leu Glu Ala Ile Val Val Ala
1               5                   10                  15
Thr Asn Pro Ser Gly Arg Leu Ile Ser Glu Leu Phe Gln Lys Leu Pro
            20                  25                  30
Ser Lys Val Gln Tyr Pro Asp Tyr Tyr Ala Ile Ile Lys Glu Pro Ile
        35                  40                  45
Asp Leu Lys Thr Ile Ala Gln Arg Ile Gln Asn Gly Ser Tyr Lys Ser
    50                  55                  60
Ile His Ala Met Ala Lys Asp Ile Asp Leu Leu Ala Lys Asn Ala Lys
65                  70                  75                  80
Thr Tyr Asn Glu Pro Gly Ser Gln Val Phe Lys Asp Ala Asn Ser Ile
                85                  90                  95
Lys Lys Ile Phe Tyr Met Lys Lys Ala Glu Ile Glu His His Glu Met
            100                 105                 110
```

<210> SEQ ID NO 28
<211> LENGTH: 112

```
<212> TYPE: PRT
<213> ORGANISM: Artificial Sequence
<220> FEATURE:
<223> OTHER INFORMATION: synthetic peptide

<400> SEQUENCE: 28

Asp Pro Ile Ala Val Cys His Glu Leu Tyr Asn Thr Ile Arg Asp Tyr
1               5                   10                  15

Lys Asp Glu Gln Gly Arg Leu Leu Cys Glu Leu Phe Ile Arg Ala Pro
            20                  25                  30

Lys Arg Asn Gln Pro Asp Tyr Tyr Glu Val Val Ser Gln Pro Ile
        35                  40                  45

Asp Leu Met Lys Ile Gln Gln Lys Leu Lys Met Glu Asp Tyr Asp Asp
    50                  55                  60

Val Asn Leu Leu Thr Ala Asp Phe Gln Leu Leu Phe Asn Asn Ala Lys
65                  70                  75                  80

Ser Tyr Tyr Lys Pro Asp Ser Pro Glu Tyr Lys Ala Ala Cys Lys Leu
                85                  90                  95

Trp Asp Leu Tyr Leu Arg Thr Arg Asn Glu Phe Val Gln Lys Gly Glu
                100                 105                 110

<210> SEQ ID NO 29
<211> LENGTH: 112
<212> TYPE: PRT
<213> ORGANISM: Artificial Sequence
<220> FEATURE:
<223> OTHER INFORMATION: synthetic peptide

<400> SEQUENCE: 29

Asp Val Ser Asn Pro Phe Tyr Gln Leu Tyr Asp Thr Val Arg Ser Cys
1               5                   10                  15

Arg Asn Asn Gln Gly Gln Leu Ile Ala Glu Pro Phe Tyr His Leu Pro
            20                  25                  30

Ser Lys Lys Lys Tyr Pro Asp Tyr Tyr Gln Gln Ile Lys Met Pro Ile
        35                  40                  45

Ser Leu Gln Gln Ile Arg Thr Lys Leu Lys Asn Gln Glu Tyr Glu Thr
    50                  55                  60

Leu Asp His Leu Glu Cys Asp Leu Asn Leu Met Phe Glu Asn Ala Lys
65                  70                  75                  80

Arg Tyr Asn Val Pro Asn Ser Ala Ile Tyr Lys Arg Val Leu Lys Leu
                85                  90                  95

Gln Gln Val Met Gln Ala Lys Lys Lys Glu Leu Ala Arg Arg Asp Asp
                100                 105                 110

<210> SEQ ID NO 30
<211> LENGTH: 112
<212> TYPE: PRT
<213> ORGANISM: Artificial Sequence
<220> FEATURE:
<223> OTHER INFORMATION: synthetic peptide

<400> SEQUENCE: 30

Asn Val Thr Leu Leu Ile Gln Glu Leu Ile His Asn Leu Phe Val Ser
1               5                   10                  15

Val Met Ser His Gln Asp Asp Glu Gly Arg Cys Tyr Ser Asp Ser Leu
            20                  25                  30

Ala Glu Ile Pro Ala Val Asp Pro Asn Phe Pro Asn Lys Pro Pro Leu
        35                  40                  45

Thr Phe Asp Ile Ile Arg Lys Asn Val Glu Asn Asn Arg Tyr Arg Arg
```

-continued

```
                50                  55                  60
Leu Asp Leu Phe Gln Glu His Met Phe Glu Val Leu Glu Arg Ala Arg
 65                  70                  75                  80

Arg Met Asn Arg Thr Asp Ser Glu Ile Tyr Glu Asp Ala Val Glu Leu
                 85                  90                  95

Gln Gln Phe Phe Ile Lys Ile Arg Asp Glu Leu Cys Lys Asn Gly Glu
            100                 105                 110

<210> SEQ ID NO 31
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 31
gagggacaga agaacccaca                                               20

<210> SEQ ID NO 32
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 32
cagttctcga cccttgcttc                                               20

<210> SEQ ID NO 33
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 33
agacagccgc atcttcttgt                                               20

<210> SEQ ID NO 34
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 34
cttgccgtgg gtagagtcat                                               20

<210> SEQ ID NO 35
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 35
agctcaccgg gctcaaggct                                               20

<210> SEQ ID NO 36
<211> LENGTH: 20
<212> TYPE: DNA
<213> ORGANISM: Artificial Sequence
<220> FEATURE:
<223> OTHER INFORMATION: synthetic oligonucleotide
```

```
<400> SEQUENCE: 36
agcagcagct ggtcgtgctc                                          20

<210> SEQ ID NO 37
<211> LENGTH: 20
<212> TYPE: DNA
<213> ORGANISM: uenArtificial Sequence
<220> FEATURE:
<223> OTHER INFORMATION: synthetic oligonucleotide

<400> SEQUENCE: 37
cggagggtca gattttgaat                                          20

<210> SEQ ID NO 38
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 38
gcccgtagca cttttgtttc                                          20
```